US012303359B2

United States Patent
Viens et al.

(10) Patent No.: US 12,303,359 B2
(45) Date of Patent: May 20, 2025

(54) LAYER FOR ABSORBENT ARTICLE

(71) Applicant: The Procter & Gamble Company, Cincinnati, OH (US)

(72) Inventors: Gerard A. Viens, Wyoming, OH (US); Christopher Philip Bewick-Sonntag, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 131 days.

(21) Appl. No.: 16/143,530

(22) Filed: Sep. 27, 2018

(65) Prior Publication Data

US 2019/0099301 A1 Apr. 4, 2019

Related U.S. Application Data

(60) Provisional application No. 62/599,193, filed on Dec. 15, 2017, provisional application No. 62/565,705, filed on Sep. 29, 2017.

(51) Int. Cl.
*A61F 13/15* (2006.01)
*A61F 13/532* (2006.01)
*A61F 13/535* (2006.01)
*A61F 13/537* (2006.01)
*D04H 1/4374* (2012.01)
(Continued)

(52) U.S. Cl.
CPC ...... *A61F 13/15203* (2013.01); *A61F 13/532* (2013.01); *A61F 13/535* (2013.01); *A61F 13/537* (2013.01); *D04H 1/4374* (2013.01); *D04H 1/43828* (2020.05); *D04H 1/43832* (2020.05); *D04H 1/43835* (2020.05); *D04H 1/43914* (2020.05); *D04H 1/465* (2013.01); *D04H 1/5412* (2020.05);
(Continued)

(58) Field of Classification Search
CPC .............. A61F 13/15203; A61F 13/537; A61F 13/532; A61F 13/535; A61F 13/472; D04H 1/43914; D04H 1/5412; D04H 1/465; D04H 1/43835; D04H 1/4374; D04H 1/559; D04H 1/498; D04H 1/43828; D04H 1/5418
See application file for complete search history.

(56) References Cited

U.S. PATENT DOCUMENTS 3,156,242 A 11/1964 Crowe, Jr.
3,881,489 A 5/1975 Hartwell
(Continued)

FOREIGN PATENT DOCUMENTS

CN 103061042 A 4/2013
EP 2692321 A1 * 2/2014 ....... A61F 13/53717
(Continued)

OTHER PUBLICATIONS

"EP2692321_Machine Translation" is a machine translation of EP-2692321-A1. (Year: 2014).*
(Continued)

*Primary Examiner* — Larissa Rowe Emrich
(74) *Attorney, Agent, or Firm* — Sarah M. DeCristofaro

(57) ABSTRACT

A carded staple fiber nonwoven comprising three or more stratums. The carded staple fiber nonwoven has a basis weight of up to about 175 gsm and includes a blend of absorbing fibers, stiffening fibers and filler fibers. The carded staple fiber nonwoven is heat stiffened and the three or more stratums are integrated without adhesives.

15 Claims, 14 Drawing Sheets

(51) Int. Cl.
  *D04H 1/4382* (2012.01)
  *D04H 1/4391* (2012.01)
  *D04H 1/46* (2012.01)
  *D04H 1/541* (2012.01)
  *D04H 1/559* (2012.01)
  *A61F 13/472* (2006.01)

(52) U.S. Cl.
  CPC ......... *D04H 1/5414* (2020.05); *D04H 1/5418* (2020.05); *D04H 1/559* (2013.01); *A61F 13/472* (2013.01)

(56) References Cited

U.S. PATENT DOCUMENTS

| | | | |
|---|---|---|---|
| 3,929,135 A | 12/1975 | Thompson | |
| 3,978,185 A | 8/1976 | Buntin et al. | |
| 3,989,867 A | 11/1976 | Sisson | |
| 4,324,246 A | 4/1982 | Mullane et al. | |
| 4,341,216 A | 7/1982 | Obenour | |
| 4,342,314 A | 8/1982 | Radel et al. | |
| 4,463,045 A | 7/1984 | Ahr et al. | |
| 4,591,523 A | 5/1986 | Thompson | |
| 4,609,518 A | 9/1986 | Curro et al. | |
| 4,629,643 A | 12/1986 | Curro et al. | |
| 4,695,422 A | 9/1987 | Curro et al. | |
| 4,713,068 A | 12/1987 | Wang et al. | |
| 4,818,800 A | 4/1989 | McDaniel et al. | |
| 4,834,735 A * | 5/1989 | Alemany | A61F 13/533 |
| | | | 428/218 |
| 4,839,216 A | 6/1989 | Curro et al. | |
| 4,950,264 A | 8/1990 | Osborn, III | |
| 4,988,344 A | 1/1991 | Reising et al. | |
| 4,988,345 A | 1/1991 | Reising | |
| 5,006,394 A | 4/1991 | Baird | |
| 5,433,715 A | 7/1995 | Tanzer et al. | |
| 5,458,835 A | 10/1995 | Wilkes et al. | |
| 5,518,801 A | 5/1996 | Chappell et al. | |
| 5,628,097 A | 5/1997 | Benson et al. | |
| 5,634,914 A | 6/1997 | Wilkes et al. | |
| 5,665,452 A | 9/1997 | Langdon et al. | |
| 5,792,404 A | 8/1998 | Cree et al. | |
| 5,820,615 A * | 10/1998 | Koczab | A61F 13/5116 |
| | | | 604/378 |
| 5,885,265 A | 3/1999 | Osborn, III et al. | |
| 5,989,688 A * | 11/1999 | Barge | D04H 3/14 |
| | | | 428/198 |
| 6,025,535 A | 2/2000 | Octavio et al. | |
| 6,066,388 A * | 5/2000 | Van Kerrebrouck | D04H 1/498 |
| | | | 428/218 |
| 6,333,108 B1 | 12/2001 | Wilkes et al. | |
| 6,436,508 B1 | 8/2002 | Ciammaichella et al. | |
| 6,462,251 B1 | 10/2002 | Cimini et al. | |
| 6,610,898 B1 | 8/2003 | Magnusson et al. | |
| 6,623,464 B2 | 9/2003 | Bewick-Sonntag et al. | |
| 6,664,439 B1 | 12/2003 | Arndt et al. | |
| 7,172,801 B2 | 2/2007 | Hoying et al. | |
| 7,402,723 B2 | 7/2008 | Stone et al. | |
| 7,410,683 B2 | 8/2008 | Curro et al. | |
| 7,553,532 B2 | 6/2009 | Turner et al. | |
| 7,648,752 B2 | 1/2010 | Hoying et al. | |
| 7,655,176 B2 | 2/2010 | Stone et al. | |
| 7,750,203 B2 | 7/2010 | Becker et al. | |
| 7,785,690 B2 | 8/2010 | Turner et al. | |
| 7,838,099 B2 | 11/2010 | Curro et al. | |
| 8,440,286 B2 | 5/2013 | Curro et al. | |
| 8,466,336 B2 | 6/2013 | Carlucci et al. | |
| 8,614,365 B2 | 12/2013 | Hammons et al. | |
| 8,704,036 B2 | 4/2014 | Hammons et al. | |
| 8,728,049 B2 | 5/2014 | Hammons et al. | |
| 9,295,593 B2 | 3/2016 | Van Malderen | |
| 9,456,932 B2 | 10/2016 | Digiacomantonio et al. | |
| 9,693,910 B2 | 7/2017 | Carlucci et al. | |
| 2001/0027303 A1 | 10/2001 | Bewick-Sonntag | |
| 2002/0034914 A1 * | 3/2002 | De Leon | D04H 1/49 |
| | | | 442/384 |
| 2005/0118916 A1 * | 6/2005 | Ducker | A61F 13/15203 |
| | | | 442/385 |
| 2005/0215155 A1 * | 9/2005 | Young | D04H 3/00 |
| | | | 442/337 |
| 2008/0249494 A1 | 10/2008 | Digiacomantonio et al. | |
| 2008/0312622 A1 | 12/2008 | Hundorf et al. | |
| 2011/0319855 A1 | 12/2011 | Lash | |
| 2014/0005622 A1 * | 1/2014 | Wirtz | A61F 13/532 |
| | | | 604/366 |
| 2014/0343523 A1 * | 11/2014 | Viens | D04H 1/4258 |
| | | | 604/370 |
| 2015/0351976 A1 * | 12/2015 | Viens | D04H 1/46 |
| | | | 604/378 |
| 2016/0340815 A1 | 11/2016 | Kipke et al. | |
| 2017/0137981 A1 | 5/2017 | Viñas Pich | |
| 2017/0258647 A1 | 9/2017 | Orr et al. | |

FOREIGN PATENT DOCUMENTS

| | | |
|---|---|---|
| FR | 2836161 B1 | 4/2004 |
| JP | 61-113812 A | 5/1986 |
| WO | WO9614037 A1 | 5/1996 |
| WO | WO9724097 A1 | 7/1997 |

OTHER PUBLICATIONS

PCT International Search Report and Written Opinion, mailed Jan. 17, 2019 (15 pages).

* cited by examiner

LAYER FOR ABSORBENT ARTICLE

CROSS REFERENCE TO RELATED APPLICATION

This application claims the benefit of U.S. Provisional Application No. 62/565,705, filed Sep. 29, 2017, and of U.S. Provisional Application No. 62/599,193, filed Dec. 15, 2017, the substances of which is incorporated herein by reference.

TECHNICAL FIELD

The present disclosure generally relates to an absorbent core for a disposable absorbent article having carded staple fiber nonwovens having improved performance characteristics.

BACKGROUND

Disposable absorbent articles such as feminine hygiene products, taped diapers, pant-type diapers and incontinence products are designed to absorb fluids from the wearer's body. Users of such disposable absorbent articles have several concerns. Leakage from products like catamenial pads, diapers, sanitary napkins, and incontinence pads is a significant concern. Comfort and the feel of the product against the wearer's body is also a concern. To provide better comfort, current disposable absorbent articles are typically provided with a topsheet that is flexible, soft feeling, and non-irritating to the wearer's skin. The topsheet does not itself hold the discharged fluid. Instead, the topsheet is fluid-permeable to allow the fluids to flow into an absorbent core.

Additionally, in regards to comfort, consumers desire a pad that is thin and flexible enough to not impair their movements while being thick and stiff enough to provide the desirable amount of protection. This objective becomes even more challenging when considering the dynamic nature of the absorbent article. As fluid enters the article, the weight, thickness, and flexibility of the absorbent article may all change. Hence, an article that may meet the desirable criteria before use may no longer be comfortable to the user after a given amount of fluid has been absorbed by the absorbent article. In addition, dependent upon the materials chosen, a thin and flexible article may be created that is not consumer suitable due to issues such as rewet. For example, one could create a flexible article using solely fluff cellulose. However, the product would likely have issues with rewet, disintegration, and possibly leakage.

As such there is a need to create an absorbent article that accounts for all the possible tradeoffs such that it is both comfortable while maintaining performance. In particular, there exists a need to create an absorbent article that balances performance and comfort.

Accordingly, the development of new and improved absorbent article and absorbent article core is of continued interest.

SUMMARY

A carded staple fiber nonwoven is disclosed. The carded staple fiber nonwoven comprises three or more stratums, the carded staple fiber nonwoven having a basis weight of up to about 175 gsm. The carded staple fiber nonwoven comprises a blend of absorbing fibers, stiffening fibers and filler fibers, wherein the carded staple fiber nonwoven is heat stiffened and wherein the three or more stratums are integrated without adhesives.

An absorbent article is also disclosed. The absorbent article comprising a topsheet, a backsheet, and an absorbent core. The absorbent core comprises a fluid acquisition/distribution layer and a fluid storage layer. The fluid acquisition/distribution layer comprises a carded staple fiber nonwoven comprising three or more stratums, wherein the fluid acquisition/distribution layer is heat stiffened. The three or more stratums are integrated without adhesives, and the fluid acquisition/distribution layer has a caliper of between about 2 millimeters and about 4 millimeters.

An absorbent article is also disclosed. The absorbent article comprising a backsheet, a fluid acquisition/distribution layer having a body facing surface and a garment facing surface and a fluid storage layer. The fluid acquisition/distribution layer comprises a carded staple fiber nonwoven comprising three or more stratums. The carded staple fiber nonwoven is heat stiffened. The three or more stratums are integrated without adhesives. The fluid acquisition/distribution layer has a caliper of between about 2 millimeters and about 4 millimeters. A stratum of the fluid acquisition/distribution layer located on the body facing surface extends beyond a second stratum of the fluid acquisition/distribution layer and is attached to the backsheet.

Figure 1:
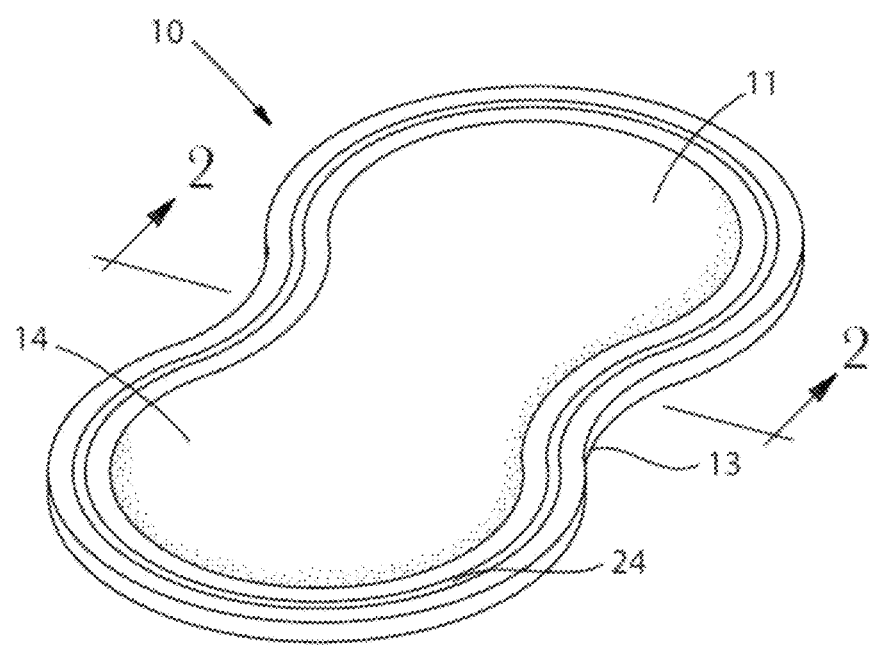
FIG. 1 is a perspective view of one example of a sanitary napkin that incorporates a carded staple fiber nonwoven.

While the specification concludes with claims particularly pointing out and distinctly claiming the subject matter that is regarded as the present invention, it is believed that the invention will be more fully understood from the following description taken in conjunction with the accompanying drawings. Some of the figures may have been simplified by the omission of selected elements for the purpose of more clearly showing other elements. Such omissions of elements in some figures are not necessarily indicative of the presence or absence of particular elements in any of the exemplary embodiments, except as may be explicitly delineated in the corresponding written description. None of the drawings are necessarily to scale.

DETAILED DESCRIPTION

As used herein, the following terms shall have the meaning specified thereafter:

"Absorbent article" refers to wearable devices, which absorb and/or contain liquid, and more specifically, refers to devices, which are placed against or in proximity to the body of the wearer to absorb and contain the various exudates discharged from the body. Absorbent articles can include diapers, training pants, adult incontinence undergarments (e.g., liners, pads and briefs) and/or feminine hygiene products.

The "longitudinal" direction is a direction running parallel to the maximum linear dimension, typically the longitudinal axis, of the article and includes directions within 450 of the longitudinal direction. "Length" of the article or component thereof, when used herein, generally refers to the size/distance of the maximum linear dimension, or typically to the size/distance of the longitudinal axis, of an article or part thereof.

The "lateral" or "transverse" direction is orthogonal to the longitudinal direction, i.e. in the same plane of the majority of the article and the longitudinal axis, and the transverse direction is parallel to the transverse axis. "Width" of the article or of a component thereof, when used herein, refers to the size/distance of the dimension orthogonal to the longitudinal direction of the article or component thereof, i.e. orthogonal to the length of the article or component thereof, and typically it refers to the distance/size of the dimension parallel of the transverse axis of the article or component.

The "Z-direction" is orthogonal to both the longitudinal and transverse directions.

"Machine Direction" or "MD" as used herein means the direction parallel to the flow of the carded staple fiber nonwoven through the nonwoven making machine and/or absorbent article product manufacturing equipment.

"Cross Machine Direction" or "CD" as used herein means the direction parallel to the width of the carded staple fiber nonwoven making machine and/or absorbent article product manufacturing equipment and perpendicular to the machine direction.

"Absorbent core" refers to a structure typically disposed between a topsheet and backsheet of an absorbent article for absorbing and containing liquid received by the absorbent article. The absorbent core may comprise one or more substrate layer(s), absorbent material disposed on the one or more substrate layer(s), and a thermoplastic adhesive composition on the absorbent material. The thermoplastic adhesive composition may be on the absorbent material and at least a portion of the one or more substrate layer. In a certain embodiment, the absorbent core would consist essentially of the one or more substrate layers, the absorbent material, the thermoplastic adhesive composition, and optionally a cover layer.

"Nonwoven material" refers to a manufactured web of directionally or randomly orientated fibers, excluding paper and products which are woven, knitted, tufted, stitch-bonded incorporating binding yarns or filaments, or felted by wet-milling, whether or not additionally needled. Nonwoven materials and processes for making them are known in the art. Generally, processes for making nonwoven materials comprise laying fibers onto a forming surface, which can comprise spunlaying, meltblowing, carding, airlaying, wet-laying, coform and combinations thereof. The fibers can be of natural or man-made origin and may be staple fibers or continuous filaments or be formed in situ.

The term "hydrophilic" describes fibers or surfaces of fibers, which are wettable by aqueous fluids (e.g., aqueous body fluids) deposited on these fibers. Hydrophilicity and wettability are typically defined in terms of contact angle and the strike-through time of the fluids, for example through a nonwoven fabric. This is discussed in detail in the American Chemical Society publication entitled, "Contact Angle, Wettability and Adhesion", edited by Robert F. Gould (Copyright 1964). A fiber or surface of a fiber is said to be wetted by a fluid (i.e., hydrophilic) when either the contact angle between the fluid and the fiber, or its surface, is less than 90°, or when the fluid tends to spread spontaneously across the surface of the fiber, both conditions are normally co-existing. Conversely, a fiber or surface of the fiber is considered to be "hydrophobic" if the contact angle is greater than 900 and the fluid does not spread spontaneously across the surface of the fiber.

The term "Pore Volume Ratio" means the ratio of the peak of the pore volume versus the pore radii curve divided by the width of the same pore radii curve at half the peak of the pore volume.

The term "Pore Volume Radius Mode" means the radius at which the peak of the pore volume versus pore radii curve occurs.

The term "Pore Volume Factor" is the product of the Pore Volume Ratio and the Pore Volume Radius Mode.

A carded staple fiber nonwoven as disclosed herein can be used in a variety of disposable absorbent articles, but is particularly useful in diapers, feminine hygiene products and incontinence products such as sanitary napkins and incontinence pads. One non-limiting embodiment of a disposable absorbent article that incorporates a carded staple fiber nonwoven as detailed herein is shown as a sanitary napkin in FIGS. 1 and 2. In another embodiment, an incontinence pad incorporates a carded staple fiber nonwoven as detailed herein. Although a sanitary napkin will be specifically illustrated and described within this application, any of the features or elements of the sanitary napkin that are disclosed are also contemplated for any other embodiment of absorbent article, including incontinence pads.

A sanitary napkin 10 can have any shape known in the art for feminine hygiene articles, including the generally symmetric "hourglass" shape as shown in FIG. 1, as well as pear shapes, ovals, oblong ovals, pill shapes, bicycle-seat shapes, trapezoidal shapes, or wedge shapes. Sanitary napkins and pantiliners can also be provided with lateral extensions known in the art as "flaps" or "wings" (not shown in FIG. 1). Such extensions can serve a number of purposes, including, but not limited to, protecting the wearer's panties from soiling and keeping the sanitary napkin secured in place. The illustrated absorbent article has a body-facing upper side that contacts the user's body during use. The opposite, garment-facing lower side contacts the user's clothing during use.

The upper side of the sanitary napkin 10 generally has a topsheet 14 that can be liquid pervious. The lower side (seen in FIGS. 2A-C) has a backsheet 16 that can generally be liquid impervious and is joined with the topsheet 14 along the peripheral edges of the sanitary napkin 10. In some embodiments of adult incontinence products not pictured herein, the topsheet and the backsheet are not joined along the edges. An absorbent core structure 18 is positioned between the topsheet 14 and the backsheet 16. The illustrated sanitary napkin 10 has a body-facing upper side 11 that contacts the user's body during use. The opposite, garment-facing lower side 13 contacts the user's clothing during use. As shown in FIG. 2A, the absorbent core structure 18 may include a fluid acquisition/distribution layer 20 and a fluid storage layer 22. The fluid acquisition/distribution layer 20 may include three or more stratums (32, 34, 36) wherein the stratums each have unique properties while being integrated to form a single layer. Two or more stratums may have the same properties within the acquisition/distribution layer. For example, an acquisition/distribution layer may have four stratums wherein the first and third stratum have the same composition and properties. Alternatively, an acquisition/distribution layer may have four stratums wherein two adjacent stratums have the same composition and properties. As shown in FIG. 2A, the fluid storage layer 22 may have a smaller width than the fluid acquisition/distribution layer 20.

As shown in FIG. 2B, the absorbent core structure 18 may include a fluid acquisition/distribution layer 20 and a storage layer 22. The fluid acquisition/distribution layer 20 may include three or more stratums (32, 34, 36) wherein the stratums each have unique properties while being integrated to form a single layer. The fluid acquisition/distribution layer having a body facing side 38 and a garment facing side 40. As shown in FIG. 2B, the fluid storage layer 22 may have an equal width than the fluid acquisition/distribution layer 20.

As shown in FIG. 2C, the absorbent core structure 18 may include a fluid acquisition/distribution layer 20 and a storage layer 22. The fluid acquisition/distribution layer 20 may include three or more stratums (32, 34, 36, 37) wherein the stratums each have unique properties while being integrated to form a single layer. As shown in FIG. 2C, the acquisition/distribution layer 20 may include the topsheet 14 as its upper stratum 32. In this manner, the upper stratum 32 may be joined with the backsheet 16 by an additional strip of material 56 thereby allowing the acquisition/distribution layer 20 to serve as the topsheet 14 of the sanitary napkin 10.

Figure 2:
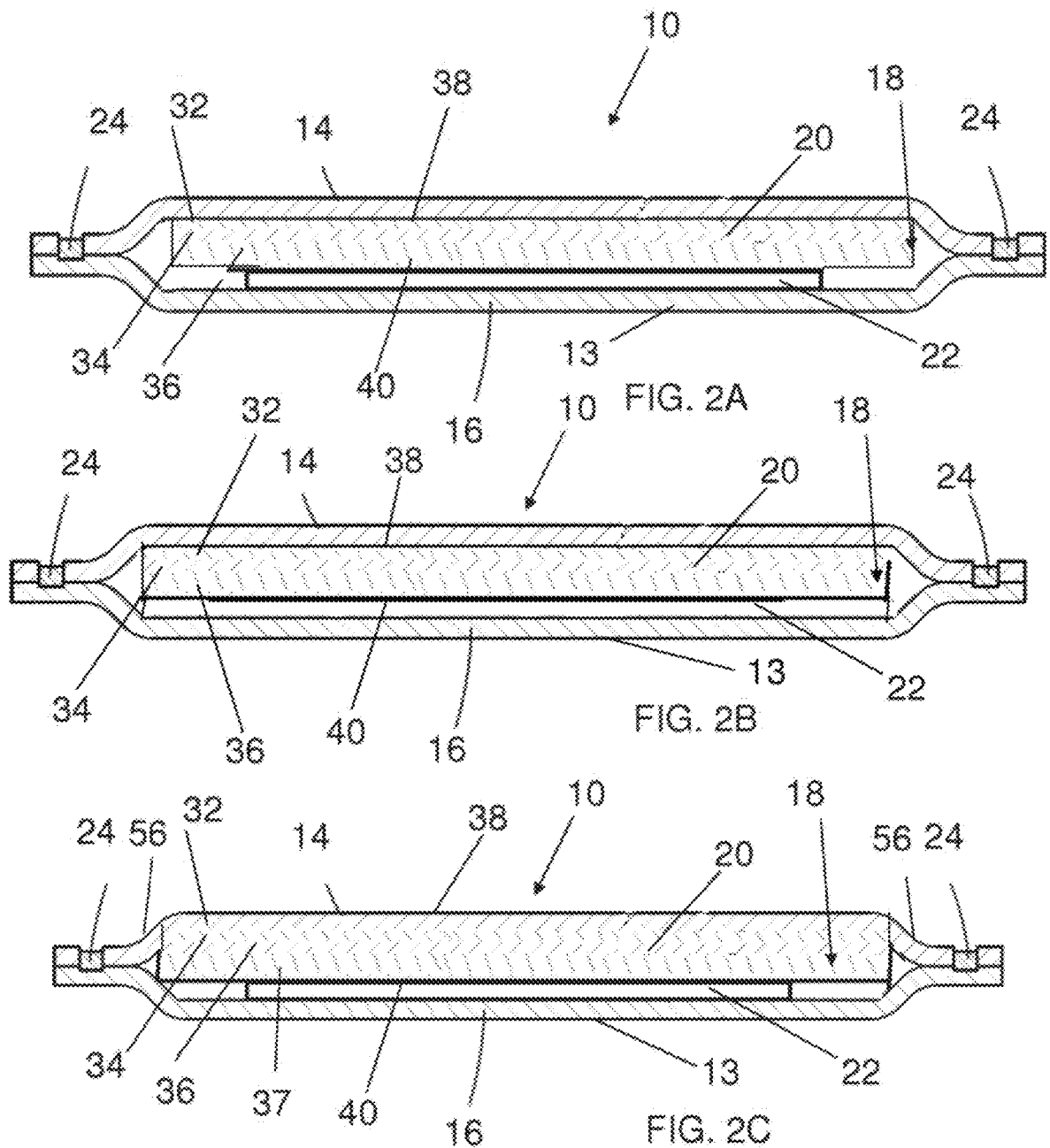
FIGS. 2A-2C are representative cross-sectional views of the sanitary napkin of FIG. 1, taken through line 2-2.

The backsheet 16 and the topsheet 14, as shown in FIGS. 1 and 2, can be secured together in a variety of ways. Adhesives manufactured by H. B. Fuller Company of St. Paul, Minn. under the designation HL-1258 or H-2031 have been found to be satisfactory. Alternatively, the topsheet 14 and the backsheet 16 can be joined to each other by heat bonding, pressure bonding, ultrasonic bonding, dynamic mechanical bonding, a crimp seal, or by any other suitable securing method. As shown in FIG. 2, a fluid impermeable crimp seal 24 can resist lateral migration ("wicking") of fluid through the edges of the product, inhibiting side soiling of the wearer's undergarments.

Figure 8:
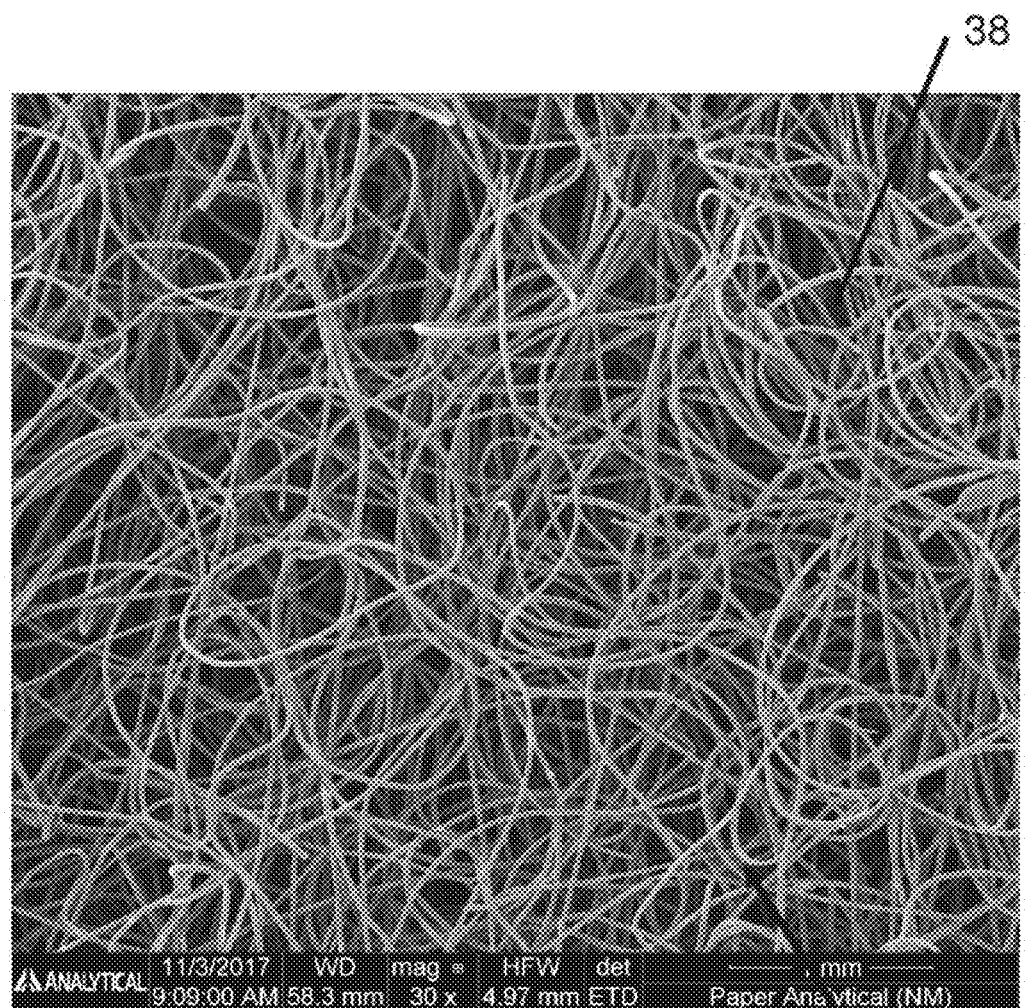
FIG. 8 is an SEM image of a first surface of a fibrous acquisition/distribution layer.
Figure 9:
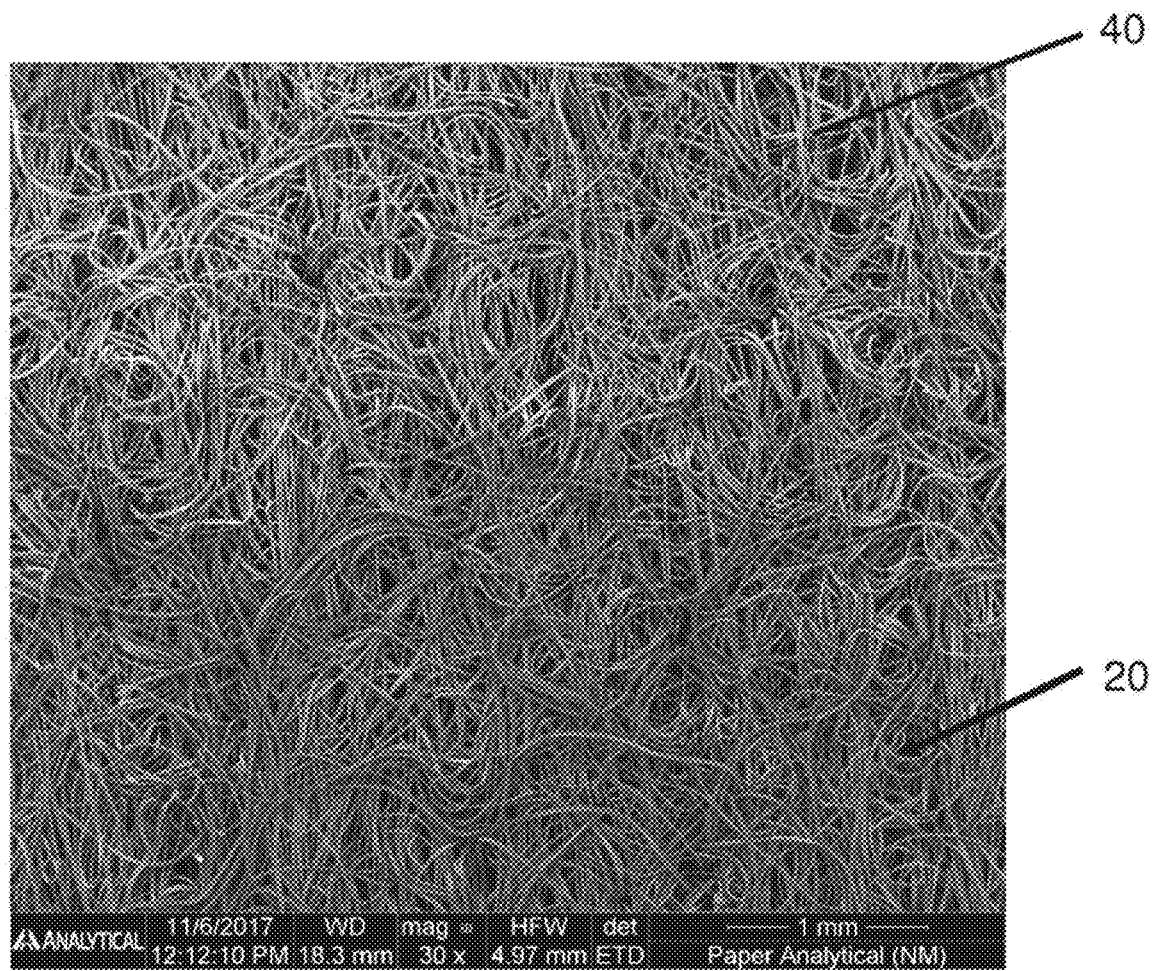
FIG. 9 is an SEM image of a second surface of a fibrous acquisition/distribution layer.
Figure 10:
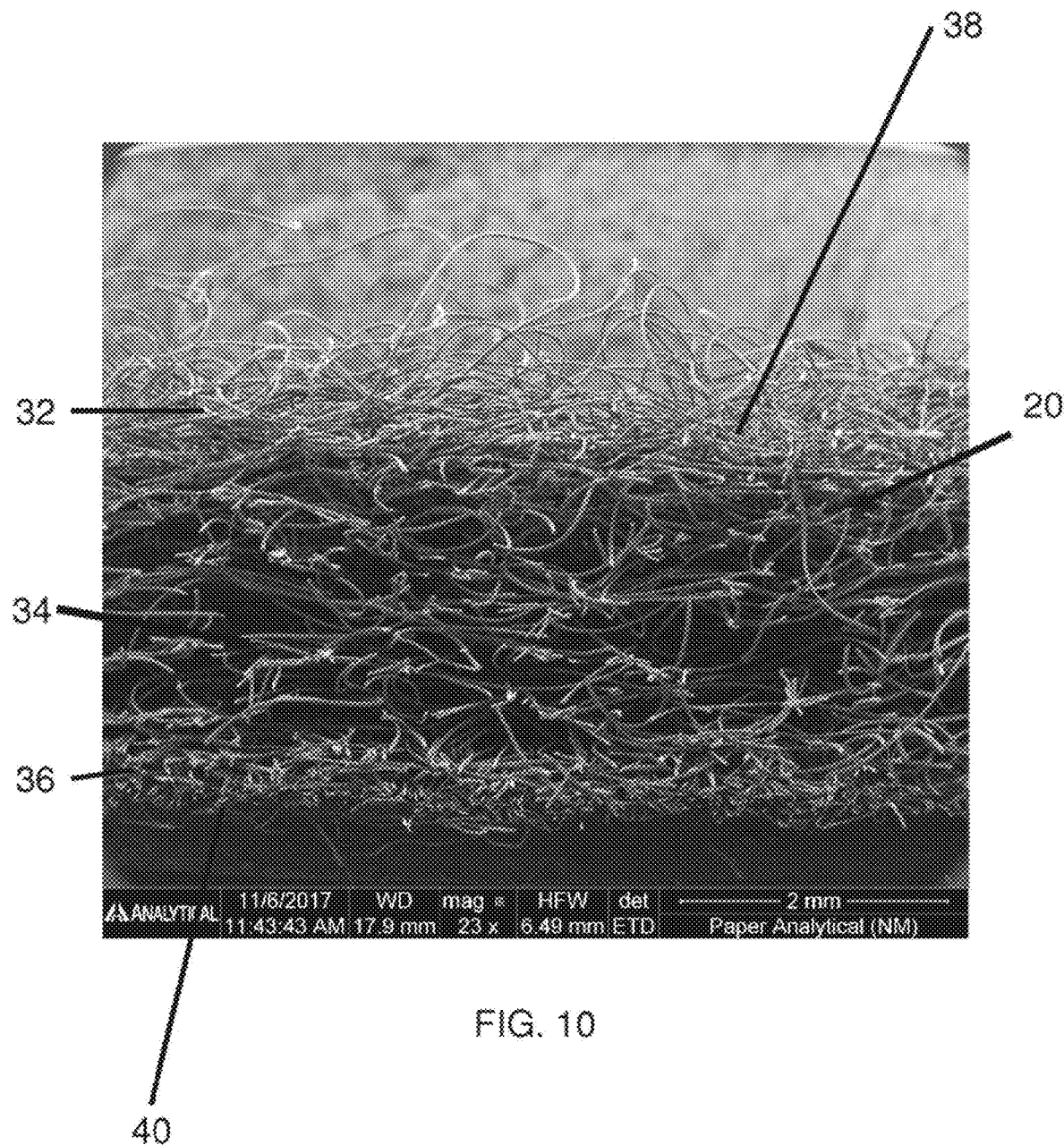
FIG. 10 is a cross section view of the fluid acquisition/distribution layer of FIG. 8.
Figure 11:
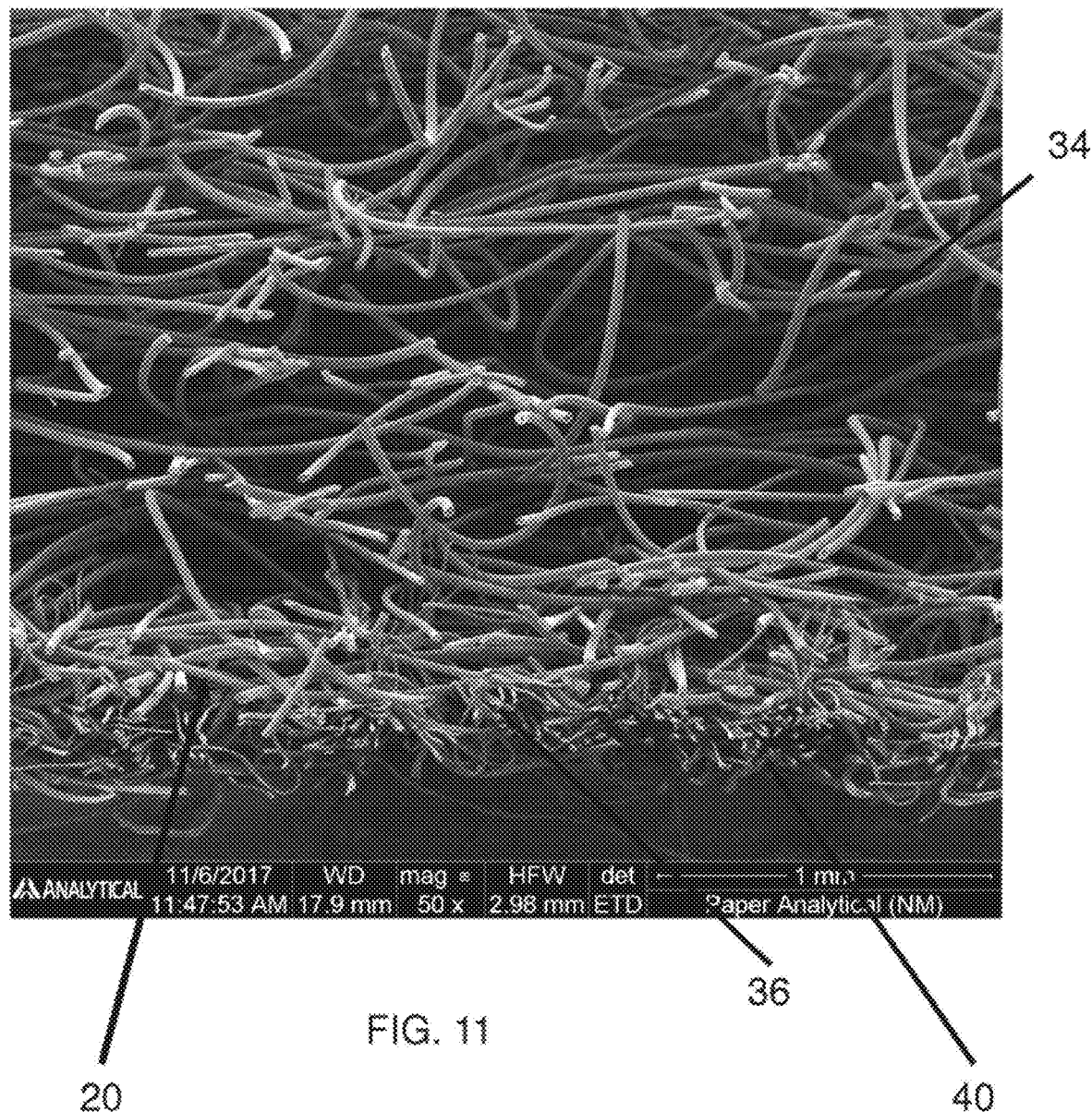
FIG. 11 is a zoomed in view of the cross-section view of FIG. 9.

The fluid acquisition/distribution layer is shown in the scanning electron microscope images of FIGS. 8-15. FIGS. 8-15 are SEMs of two different examples of embodiment 2 of Table 1. FIG. 8 shows the body facing side 38 of a fluid acquisition/distribution layer 20. FIG. 9 shows the garment facing side 40 of a fluid acquisition/distribution layer 20. FIG. 10 shows a fluid acquisition/distribution layer 20 which is a cross section of FIG. 8. The fluid acquisition/distribution layer 20 may include three or more stratums (32, 34, 36) wherein the stratums each have unique properties while being integrated to form a single layer. The fluid acquisition/distribution layer has a body facing side 38 and a garment facing side 40. FIG. 11 shows a magnified version of a portion of FIG. 10. As shown in FIG. 11, the fluid acquisition/distribution layer 20 has a garment facing side 40 and a plurality of stratums (34, 36).

Figure 12:
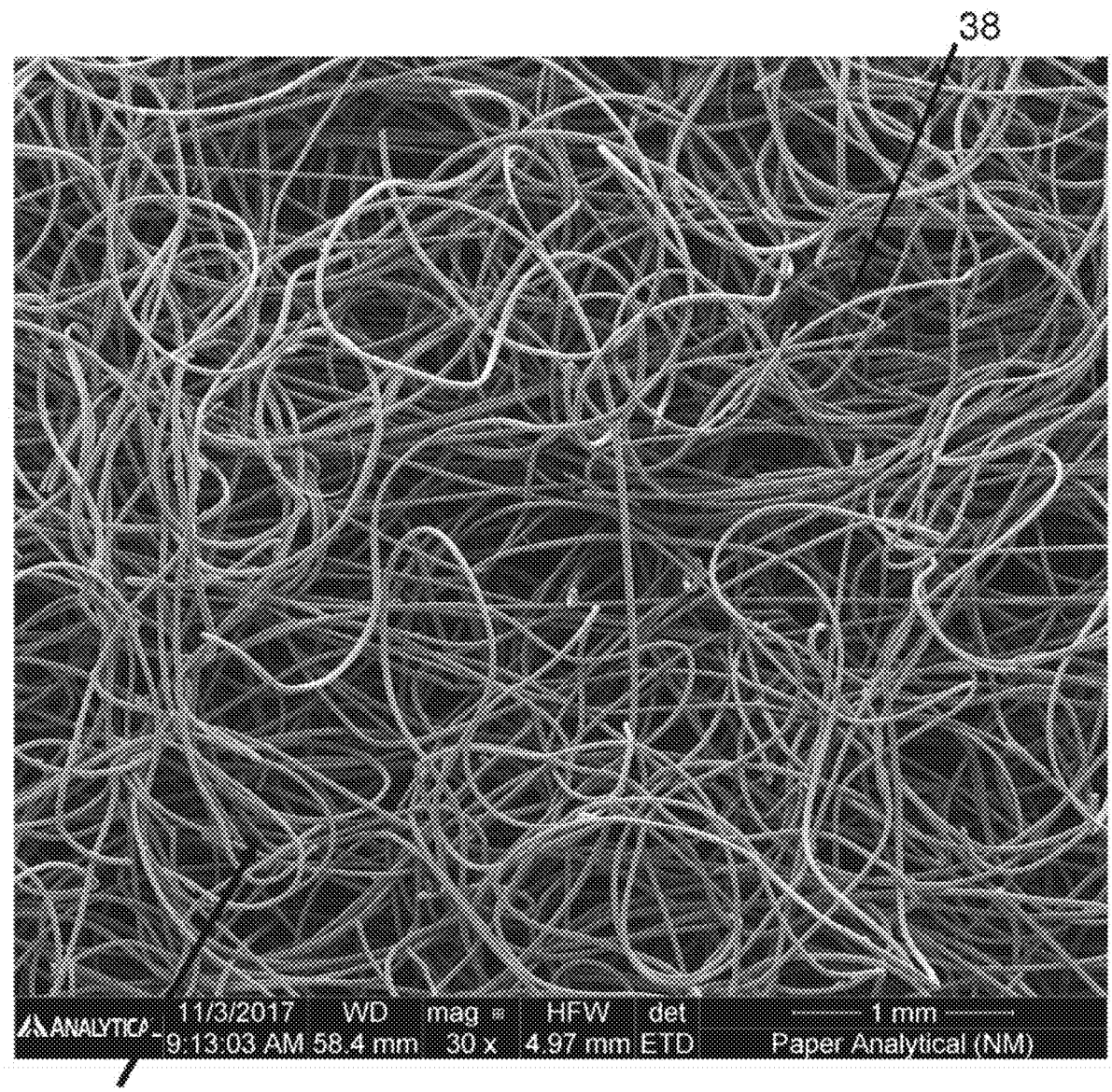
FIG. 12 is an SEM image of a first surface of a fibrous acquisition/distribution layer.
Figure 13:
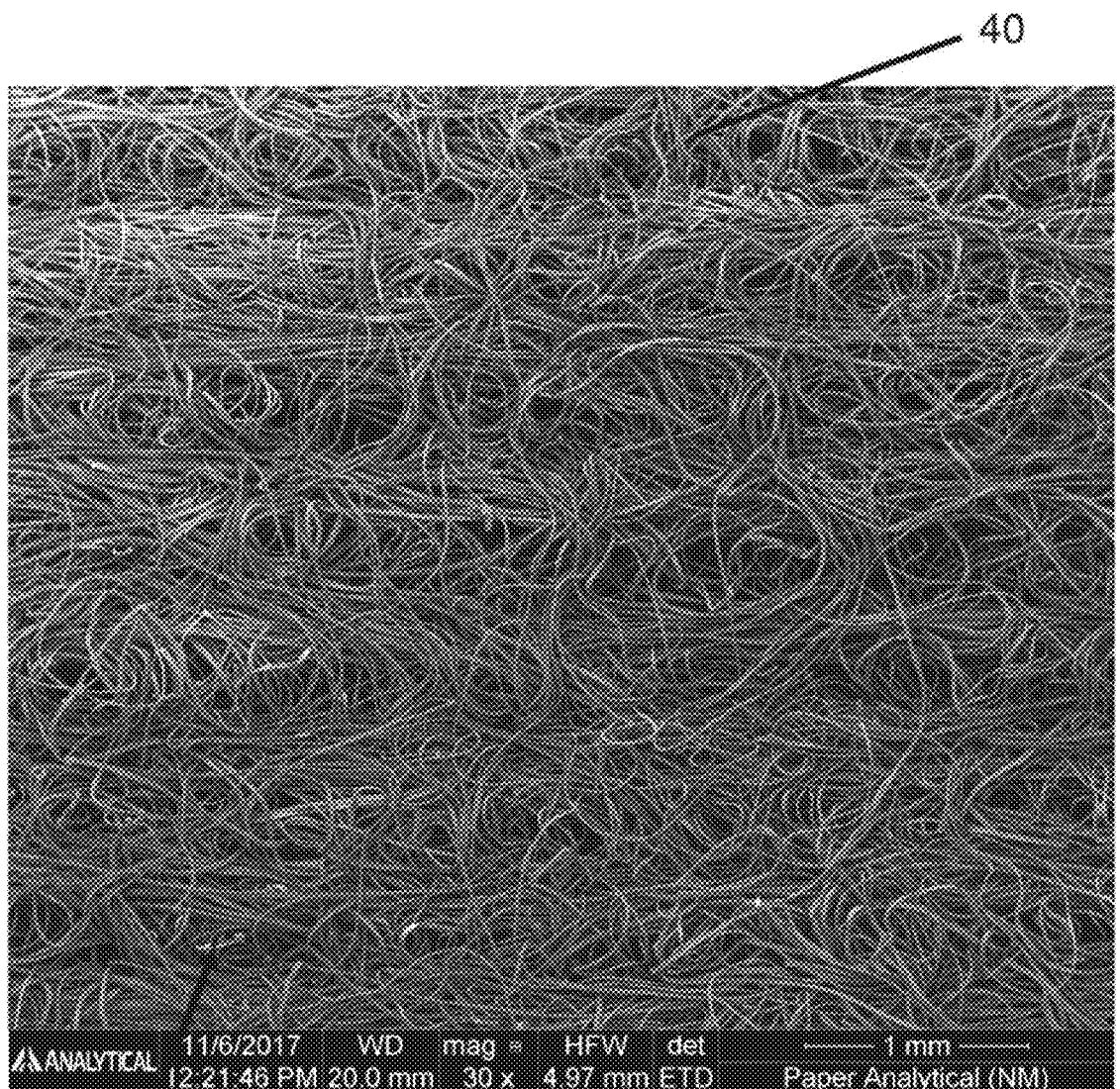
FIG. 13 is an SEM image of a second surface of a fibrous acquisition/distribution layer.
Figure 14:
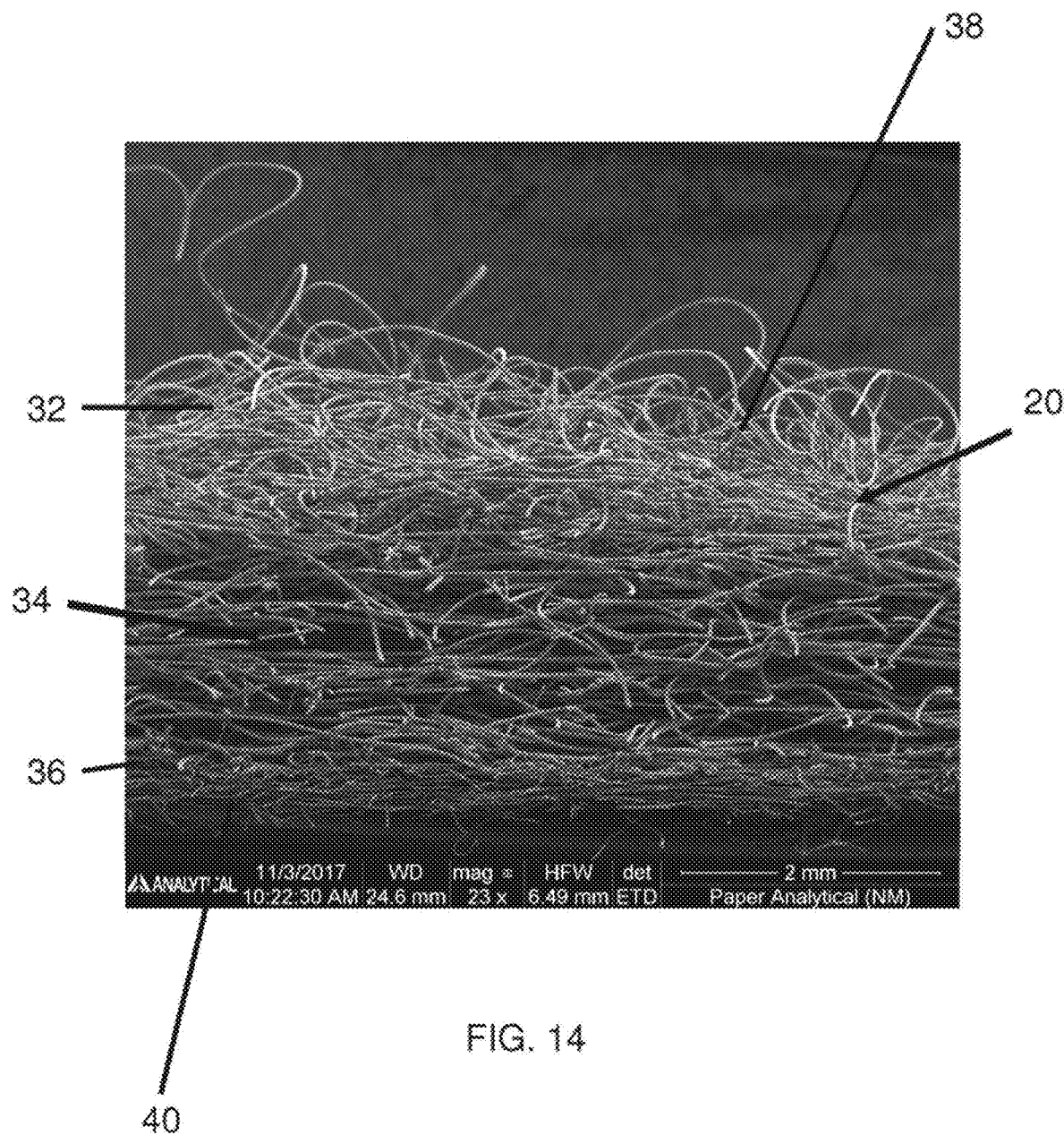
FIG. 14 is a cross section view of the fluid acquisition/distribution layer of FIG. 12.
Figure 15:
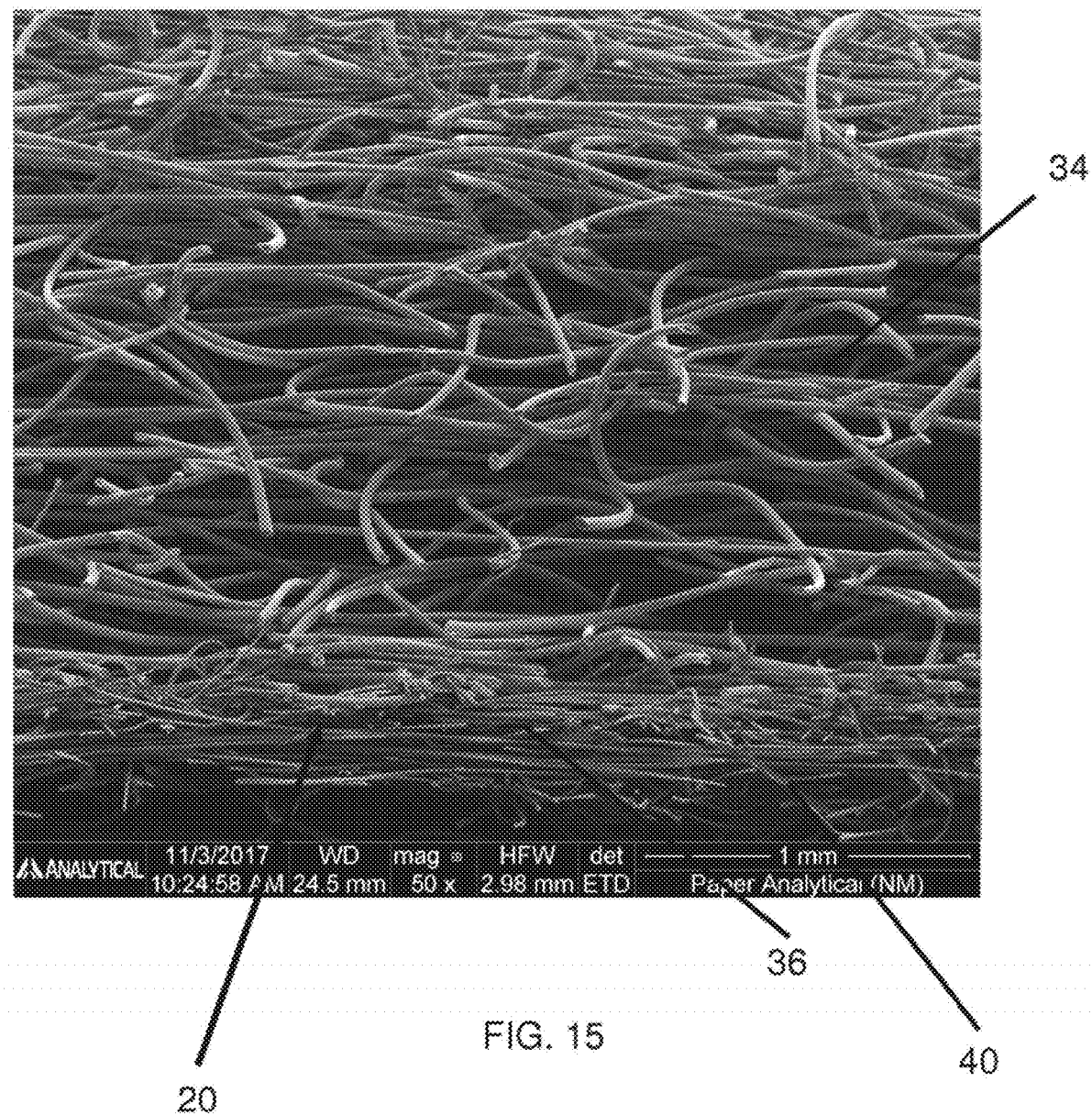
FIG. 15 is a zoomed in view of the cross-section view of FIG. 12.

FIG. 12 shows the body facing side 38 of a fluid acquisition/distribution layer 20. FIG. 13 shows the garment facing side 40 of a fluid acquisition/distribution layer 20. FIG. 14 shows a fluid acquisition/distribution layer 20 which is a cross section of FIG. 12. The fluid acquisition/distribution layer 20 may include three or more stratums (32, 34, 36) wherein the stratums each have unique properties while being integrated to form a single layer. The fluid acquisition/distribution layer has a body facing side 38 and a garment facing side 40. FIG. 15 shows a magnified version of a portion of FIG. 14. As shown in FIG. 15, the fluid acquisition/distribution layer 20 has a garment facing side 40 and a plurality of stratums (34, 36).

As is typical for sanitary napkins and the like, the sanitary napkin 10 of the present disclosure can have panty-fastening adhesive disposed on the garment-facing side of backsheet 16. The panty-fastening adhesive can be any of known adhesives used in the art for this purpose, and can be covered prior to use by a release paper, as is well known in the art. If flaps or wings are present, a panty fastening adhesive can be applied to the garment facing side so as to contact and adhere to the underside of the wearer's panties.

Topsheet

The topsheet 14 of the sanitary napkin 10 may be joined to the backsheet 16 by attachment methods (not shown) such as those well known in the art. Suitable attachment methods are described with respect to joining the backsheet 16 to the absorbent core structure 18. The topsheet 14 and the backsheet 16 may be joined directly to each other in the sanitary napkin periphery and may be indirectly joined together by directly joining them to the absorbent core structure 18 or additional optional layers within the chassis like a fluid acquisition/distribution layer which spans the entire or partial area of the article. This indirect or direct joining may be accomplished by attachment methods which are well known in the art.

The absorbent article may comprise any known or otherwise effective topsheet, such as one which is compliant, soft feeling, and non-irritating to the wearer's skin. Suitable topsheet materials include a liquid pervious material that is oriented towards and contacts the body of the wearer permitting bodily discharges to rapidly penetrate through it without allowing fluid to flow back through the topsheet to the skin of the wearer. The topsheet, while being capable of allowing rapid transfer of fluid through it, also provides for the transfer or migration of the lotion composition onto an external or internal portion of a wearer's skin. A suitable topsheet can be made of various materials such as woven and nonwoven materials; apertured film materials including apertured formed thermoplastic films, apertured plastic films, and fiber-entangled apertured films; hydro-formed thermoplastic films; porous foams; reticulated foams; reticulated thermoplastic films; thermoplastic scrims; or combinations thereof.

Apertured film materials suitable for use as the topsheet include those apertured plastic films that are non-absorbent and pervious to body exudates and provide for minimal or no flow back of fluids through the topsheet. Nonlimiting examples of other suitable formed films, including apertured and non-apertured formed films, are more fully described in U.S. Pat. No. 3,929,135, issued to Thompson on Dec. 30, 1975; U.S. Pat. No. 4,324,246, issued to Mullane et al. on Apr. 13, 1982; U.S. Pat. No. 4,342,314, issued to Radel et al. on Aug. 3, 1982; U.S. Pat. No. 4,463,045, issued to Ahr et al. on Jul. 31, 1984; U.S. Pat. No. 5,006,394, issued to Baird on Apr. 9, 1991; U.S. Pat. No. 4,609,518, issued to Curro et al. on Sep. 2, 1986; and U.S. Pat. No. 4,629,643, issued to Curro et al. on Dec. 16, 1986. Commercially available formed filmed topsheets include those topsheet materials marketed by the Procter & Gamble Company (Cincinnati, Ohio) under the DRI-WEAVE® tradename.

Nonlimiting examples of woven and nonwoven materials suitable for use as the topsheet include fibrous materials made from natural fibers, modified natural fibers, synthetic fibers, or combinations thereof. These fibrous materials can be either hydrophilic or hydrophobic, but it is preferable that the topsheet be hydrophobic or rendered hydrophobic. As an option, portions of the topsheet can be rendered hydrophilic, by the use of any known method for making topsheets containing hydrophilic components. One such method include treating an apertured film component of a nonwoven/apertured thermoplastic formed film topsheet with a surfactant as described in U.S. Pat. No. 4,950,264, issued to Osborn on Aug. 21, 1990. Other suitable methods describing a process for treating the topsheet with a surfactant are disclosed in U.S. Pat. Nos. 4,988,344 and 4,988,345, both issued to Reising et al. on Jan. 29, 1991. The topsheet may have hydrophilic fibers, hydrophobic fibers, or combinations thereof.

A particularly suitable topsheet comprises staple length polypropylene fibers having a denier of about 1.5, such as Hercules type 151 polypropylene marketed by Hercules, Inc. of Wilmington, Del. As used herein, the term "staple length fibers" refers to those fibers having a length of at least about 15.9 mm (0.62 inches).

When the topsheet comprises a nonwoven fibrous material in the form of a nonwoven web, the nonwoven web may be produced by any known procedure for making nonwoven webs, nonlimiting examples of which include spunbonding, carding, wet-laid, air-laid, meltblown, needle-punching, mechanical entangling, thermo-mechanical entangling, and hydroentangling. A specific example of a suitable meltblown process is disclosed in U.S. Pat. No. 3,978,185, to Buntin et al., issued Aug. 31, 1976. The nonwoven may be compression resistant as described in U.S. Pat. No. 7,785,690 entitled "Compression Resistant Nonwovens" issued on Aug. 31, 2010. The nonwoven web may have loops as described in U.S. Pat. No. 7,838,099 entitled "Looped Nonwoven Web" issued on Nov. 23, 2010.

Other suitable nonwoven materials include low basis weight nonwovens, that is, nonwovens having a basis weight of from about 18 g/m$^2$ to about 25 g/m$^2$. An example of such a nonwoven material is commercially available under the tradename P-8 from Veratec, Incorporation, a division of the International Paper Company located in Walpole, Massachusetts. Other nonwovens are described in U.S. Pat. Nos. 5,792,404 and 5,665,452.

The topsheet may comprise tufts as described in U.S. Pat. No. 8,728,049 entitled "Absorbent Article Having a Tufted Topsheet" issued on May 20, 2014, U.S. Pat. No. 7,553,532 entitled "Tufted Fibrous Web" issued on Jun. 30, 2009, U.S. Pat. No. 7,172,801 entitled "Tufted Laminate Web" issued on Feb. 6, 2007, or U.S. Pat. No. 8,440,286 entitled "Capped Tufted Laminate Web" issued on May 14, 2013. The topsheet may have an inverse textured web as described in U.S. Pat. No. 7,648,752 entitled "Inverse Textured Web" issued on Jan. 19, 2010. Tufts are also described in U.S. Pat. No. 7,410,683 entitled "Tufted Laminate Web" issued on Aug. 12, 2008.

The topsheet may have a pattern of discrete hair-like fibrils as described in U.S. Pat. No. 7,655,176 entitled "Method of Making a Polymeric Web Exhibiting A Soft and Silky Tactile Impression" issued on Feb. 2, 2010 or U.S. Pat. No. 7,402,723 entitled "Polymeric Web Exhibiting A Soft And Silky Tactile Impression" issued on Jul. 22, 2008.

The topsheet may comprise one or more structurally modified zones as described in U.S. Pat. No. 8,614,365 entitled "Absorbent Article" issued on Dec. 24, 2013. The topsheet may have one or more out of plane deformations as described in U.S. Pat. No. 8,704,036 entitled "Sanitary Napkin for Clean Body Benefit" issued on Apr. 22, 2014. The topsheet may have a masking composition as described in U.S. Pat. No. 6,025,535 entitled "Topsheet For Absorbent Articles Exhibiting Improved Masking Properties" issued on Feb. 15, 2000.

Another suitable topsheet or a topsheet combined with a fluid acquisition/distribution layer may be formed from a three-dimensional substrate as detailed in a U.S. provisional patent application No. 62/306,676 filed on Mar. 11, 2016 in the name of Jill M. Orr and entitled "A Three-Dimensional Substrate Comprising a Tissue Layer". This three-dimensional substrate has a first surface, a second surface, land areas and also comprises three-dimensional protrusions extending outward from the second surface of the three-dimensional substrate, wherein the three-dimensional protrusions are surrounded by the land areas. The substrate is a laminate comprising at least two layers in a face to face relationship, the second layer is a tissue layer facing outward from the second surface of the three-dimensional substrate, and the tissue layer comprises at least 80% pulp fibers by weight of the tissue layer.

The topsheet may have one or more layers, for example a spunbond-meltblown-spunbond material. The topsheet may be apertured, may have any suitable three-dimensional features, and/or may have a plurality of embossments (e.g., a bond pattern). The topsheet may be apertured by overbonding a material and then rupturing the overbonds through ring rolling, such as disclosed in U.S. Pat. No. 5,628,097, to Benson et al., issued on May 13, 1997. Additional lateral extensibility in the chassis (i.e., in the topsheet and/or the backsheet) may be provided in a variety of ways. For example, either the topsheet or backsheet may be pleated by any of many known methods. Alternatively, all or a portion of the chassis (i.e., also the topsheet and/or backsheet) may be made of a formed web material or a formed laminate of web materials like those described in U.S. Pat. No. 5,518,801 issued on 21 May 1996 in the name of Chappell et al. Such a formed web material includes distinct laterally extending regions in which the original material has been altered by embossing or another method of deformation to create a pattern of generally longitudinally oriented alternating ridges and valleys. The formed web material also includes laterally extending unaltered regions located between the laterally extending altered regions.

Backsheet

The backsheet may be positioned adjacent a garment-facing surface of the absorbent core and may be joined thereto by attachment methods (not shown) such as those well known in the art. For example, the backsheet may be secured to the absorbent core by a uniform continuous layer of adhesive, a patterned layer of adhesive, or an array of separate lines, spirals, or spots of adhesive. Alternatively, the attachment methods may comprise using heat bonds, pressure bonds, ultrasonic bonds, dynamic mechanical bonds, or any other suitable attachment methods or combinations of these attachment methods as are known in the art. Forms of the present disclosure are also contemplated wherein the absorbent core is not joined to the backsheet, the topsheet, or both.

The backsheet may be impervious, or substantially impervious, to liquids (e.g., urine) and may be manufactured from a thin plastic film, although other flexible liquid impervious materials may also be used. As used herein, the term "flexible" refers to materials which are compliant and will readily conform to the general shape and contours of the human body. The backsheet may prevent, or at least inhibit, the exudates absorbed and contained in the absorbent core from wetting articles of clothing which contact the absorbent article such as undergarments. However, in some instances, the backsheet may permit vapors to escape from the absorbent core 205 (i.e., is breathable) while in other instances the backsheet may not permit vapors to escape (i.e., non-breathable). Thus, the backsheet may comprise a polymeric film such as thermoplastic films of polyethylene or polypropylene. A suitable material for the backsheet is a thermoplastic film having a thickness of from about 0.012 mm (0.5 mil) to about 0.051 mm (2.0 mils), for example. Any suitable backsheet known in the art may be utilized with the present invention.

The backsheet acts as a barrier to any absorbed bodily fluids that may pass through the absorbent core to the garment surface thereof with a resulting reduction in risk of staining undergarments or other clothing. Further, the barrier properties of the backsheet permit manual removal, if a wearer so desires, of the interlabial absorbent article with reduced risk of hand soiling. A preferred material is a soft, smooth, compliant, liquid and vapor pervious material that provides for softness and conformability for comfort, and is low noise producing so that movement does not cause unwanted sound.

The backsheet may comprise a wet laid fibrous assembly having a temporary wet strength resin incorporated therein as described in U.S. Pat. No. 5,885,265 (Osborn, III.) issued Mar. 23, 1999. The backsheet may further be coated with a water resistant resinous material that causes the backsheet to become impervious to bodily fluids without impairing the spreading of adhesive materials thereon.

Another suitable backsheet material is a polyethylene film having a thickness of from about 0.012 mm (0.5 mil) to about 0.051 mm (2.0 mils). The backsheet may be embossed and/or matte finished to provide a more clothlike appearance. Further, the backsheet may permit vapors to escape from the absorbent core structure 18 (i.e., the backsheet is breathable) while still preventing body fluids from passing through the backsheet. A preferred microporous polyethylene film which is available from Tredegar Corporation, Virginia, USA, under Code No. XBF-1 12W.

For a stretchable but non-elastic backsheet, one material can be used is a hydrophobic, stretchable, spun laced, non-woven material having a basis weight of from about 30 to 40 g/m2, formed of polyethylene terephthalate or polypropylene fibers. This material is breathable, i.e. permeable to water vapour and other gases.

For an elastic backsheet, one material which can be used is an elastic film sold under the trade mark EXX500 by Exxon Corporation. The material of this film is formed from an elastomeric base composition consisting of a styrene block copolymer. However, this material is not breathable. Another material which can be used for an elastic backsheet is a plastic film that has been subjected to a process that provides it with elastic-like properties without attaching elastic strands to the film, and may for example comprise a formed film made in accordance with U.S. Pat. No. 4,342,314 (Radel et al) and U.S. Pat. No. 4,463,045 (Ahr et al).

Suitable breathable backsheets for use herein include all breathable backsheets known in the art. In principle, there are two types of breathable backsheets, single layer breathable backsheets which are breathable and impervious to liquids and backsheets having at least two layers, which in combination provide both breathability and liquid imperviousness. Suitable single layer breathable backsheets for use herein include those described for example in GB A 2184 389, GB A 2184 390, GB A 2184 391, U.S. Pat. No. 4,591,523, 3,989,867, 3,156,242 and WO 97/24097.

The backsheet may have two layers: a first layer comprising a gas permeable aperture formed film layer and a second layer comprising a breathable microporous film layer as described in U.S. Pat. No. 6,462,251 (Cimini) issued Oct. 8, 2002. Suitable dual or multi-layer breathable backsheets for use herein include those exemplified in U.S. Pat. Nos. 3,881,489, 4,341,216, 4,713,068, 4,818,600, EP 203 821, EP 710 471, EP 710 472, and EP 793 952.

The backsheet may be a relatively hydrophobic 18 grams per square meter (gsm) spunbonded nonwoven web of 2 denier polypropylene fibers. The backsheet may also be a laminate as is known in the art.

The backsheet may be vapor permeable as described in U.S. Pat. No. 6,623,464 (Bewick-Sonntag) issued Sep. 23, 2003 or U.S. Pat. No. 6,664,439 (Arndt) issued Dec. 16, 2003. The backsheet can be formed from any vapor permeable material known in the art. Backsheet can be a microporous film, an apertured formed film, or other polymer film that is vapor permeable, or rendered to be vapor permeable, as is known in the art.

The backsheet may be a nonwoven web having a basis weight between about 20 gsm and about 50 gsm. In one embodiment, the backsheet is a relatively hydrophobic 23 gsm spunbonded nonwoven web of 4 denier polypropylene fibers available from Fiberweb Neuberger, under the designation F102301001. The backsheet may be coated with a non-soluble, liquid swellable material as described in U.S. Pat. No. 6,436,508 (Ciammaichella) issued Aug. 20, 2002. The backsheet has a garment-facing side and an opposite body-facing side. The garment-facing side of the backsheet comprises a non-adhesive area and an adhesive area. The adhesive area may be provided by any conventional means. Pressure sensitive adhesives have been commonly found to work well for this purpose.

Still referring to FIG. 1, the absorbent core structure 18 of a sanitary napkin serves to store bodily fluids discharged during use. The absorbent core structure 18 can be manufactured in a wide variety of sizes and shapes, and may be profiled to have different thickness, hydrophilic gradients, superabsorbent gradients, densities, or average basis weights at different positions across the face of the sanitary napkin 10.

As shown in FIGS. 2A-2C, the absorbent core structure 18 can have a fluid acquisition/distribution layer 20 as well as a secondary storage layer 22. The fluid acquisition/distribution layer may transfer the received fluid both downwardly and laterally, and generally has more permeability than the secondary storage layer. The carded staple fiber nonwovens detailed herein may also assist in transferring the received fluid both downwardly and laterally to the core.

The secondary storage layer can contain conventional absorbent materials. In addition to conventional absorbent materials such as creped cellulose wadding, fluffed cellulose fibers, Rayon fibers, wood pulp fibers also known as airfelt, and textile fibers, the secondary storage layer often includes superabsorbent material that imbibes fluids and form hydrogels. Such materials are also known as absorbent gelling materials (AGM), and may be included in particle form. AGM is typically capable of absorbing large quantities of body fluids and retaining them under moderate pressures. Synthetic fibers including cellulose acetate, polyvinyl fluoride, polyvinylidene chloride, acrylics (such as ORLON), polyvinyl acetate, non-soluble polyvinyl alcohol, polyethylene, polypropylene, polyamides (such as nylon), polyesters, bicomponent fibers, tricomponent fibers, mixtures thereof and the like can also be used in the secondary storage layer. The secondary storage layer can also include filler materials, such as PERLITE, diatomaceous earth, VERMICULITE, or other suitable materials, that lower rewet problems.

The secondary storage layer or fluid storage layer may have absorbent gelling material (agm) in an uniform distribution or may have agm in a non-uniform distribution. The agm may be in the in the form of channels, pockets, stripes, criss-cross patterns, swirls, dots, or any other pattern, either two or three dimensional, that can be imagined by man.

In some embodiments, portions of the secondary storage layer 22 of the absorbent core structure 18 can be formed only of superabsorbent material, or can be formed of superabsorbent materials dispersed in a suitable carrier such as cellulose fibers in the form of fluff or stiffened fibers. One example of a non-limiting absorbent core structure 18 is a first layer formed only of superabsorbent material that is disposed on a second layer that is formed from a dispersion of superabsorbent material within cellulose fibers.

Detailed examples of absorbent cores formed of layers of superabsorbent material and/or layers of superabsorbent material dispersed within cellulose fibers that may be utilized in the absorbent articles (e.g., sanitary napkins, incontinence products) detailed herein are disclosed in U.S. Patent Publication No. 2010/0228209 A1. Absorbent cores comprising relatively high amounts of SAP with various core designs are disclosed in U.S. Pat. No. 5,599,335 to Goldman et al., EP 1,447,066 to Busam et al., WO 95/11652 to Tanzer et al., U.S. Pat. Publ. No. 2008/0312622A1 to Hundorf et al., WO 2012/052172 to Van Malderen, U.S. Pat. No. 8,466,336 to Carlucci, and U.S. Pat. No. 9,693,910 to Carlucci. These may be used to configure the secondary storage layer.

Figure 4:
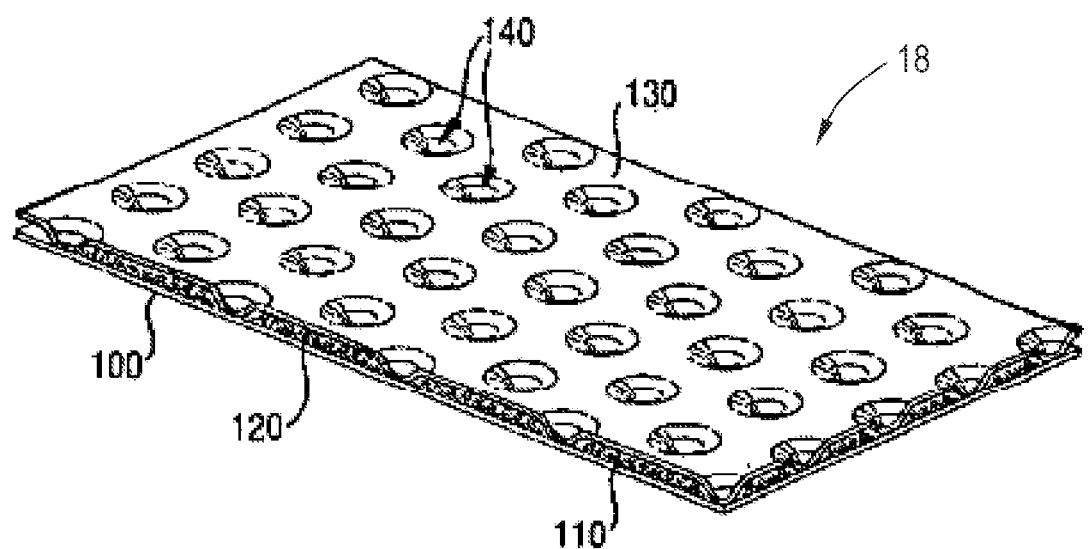
FIG. 4 shows a perspective view of an exemplary absorbent core.
Figure 5A:
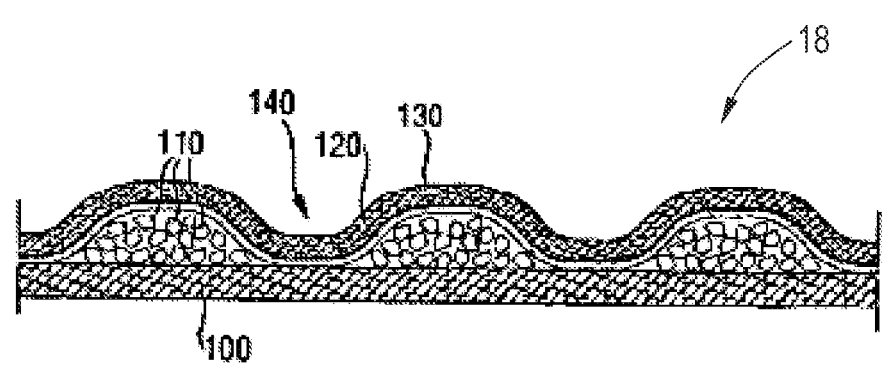
FIGS. 5A and 5B are schematic cross sections of two embodiments of an absorbent core.
Figure 5B:
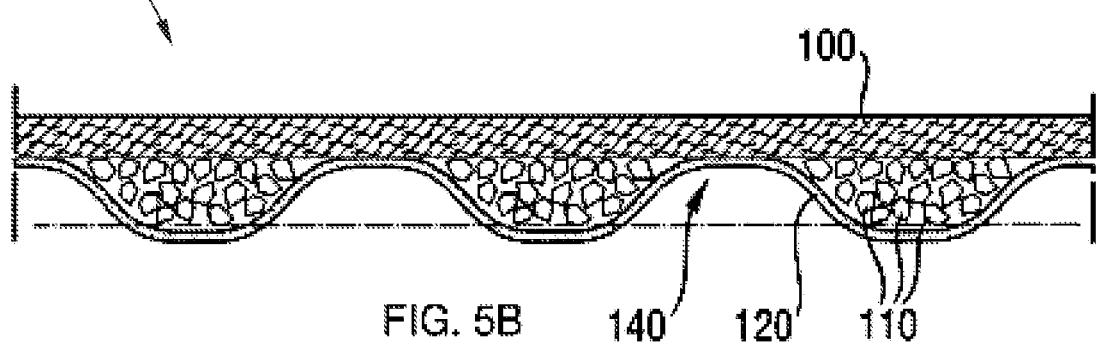

As shown for example in the embodiments of FIGS. 4 and 5A-B, the absorbent core structure 18 can comprise a substrate layer 100, a layer of absorbent polymer material 110, a layer of adhesive 120, and a cover layer 130. As shown in FIG. 5B, the storage layer may be used as shown in FIG. 5A or upside down as shown in FIG. 5B. The terms "substrate" and "cover", referred to the substrate layer 100 and to the cover layer 130, reflect one possible orientation of the absorbent core structure 18 when for example incorporated into an absorbent article, such as for example the sanitary napkin 10 shown in FIG. 1, wherein the substrate layer 100 can actually constitute a substrate layer in that it is a bottom layer, i.e. for example closer to the backsheet 16, and the cover layer 130 can actually constitute a cover layer in that it is a top layer, i.e. closer to the topsheet 14. Typically the adhesive can be a hot melt adhesive. According to the present invention, the layer of adhesive 120 can be typically for example a layer of fiberized hot melt adhesive 120. The substrate layer 100 can for example comprise a fibrous material. Suitable materials for the cover layer can be for example nonwoven materials.

The substrate layer 100, the layer of absorbent polymer material 110, the layer of adhesive 120, and the cover layer 130 each comprise a first surface and a second surface. Conventionally, in all the sectional views illustrated in the attached drawings the first surface of each layer is meant to correspond to the top surface, in turn, unless stated otherwise, corresponding to the wearer facing surface of the article incorporating the absorbent storage layer, while the second surface corresponds to the bottom surface, hence in turn the garment facing surface.

In general, in the storage layer of the present invention the arrangement of the various layers is such that the second surface of the layer of absorbent polymer material 110 is facing the first surface of the substrate layer 100, the first surface of the layer of absorbent polymer material 110 is facing the second surface of the layer of adhesive 120, and the second surface of the cover layer 130 is facing the first surface of the layer of adhesive 120.

As shown in FIGS. 5A-B, portions of the first surface of the substrate layer 100 can be in contact with the layer of absorbent polymer material 110. This layer of absorbent polymer material 110 comprises a first surface and a second surface, and can be typically a uniform or non-uniform layer, wherein by "uniform" or "non-uniform" it is meant that the absorbent polymer material 110 can be distributed over the substrate layer 100 respectively with uniform or non-uniform basis weight over the area interested by the distribution. Conversely, the second surface of the layer of absorbent polymer material 110 can be in at least partial contact with the first surface of the substrate layer 100. According to the present invention, the layer of absorbent polymer material 110 can also be a discontinuous layer that is a layer typically comprising openings, i.e. areas substantially free of absorbent polymer material, which in certain embodiments can be typically completely surrounded by areas comprising absorbent polymer material. Typically these openings have a diameter or largest span of less than 10 mm, or less than 5 mm, or 3 mm, or 2 mm, or 1.5 mm and of more than 0.5 mm, or 1 mm. At least portions of the second surface of the layer of absorbent polymer material 110 can be in contact with at least portions of the first surface of the substrate layer 100. The first surface of the layer of absorbent polymer material 110 defines a certain height of the layer of absorbent polymer material above the first surface of the layer of substrate 100. When the layer of absorbent polymer material 110 is provided as a non-uniform layer, typically for example as a discontinuous layer, at least some portions of the first surface of the substrate layer 100 can be not covered by absorbent polymer material 110. The absorbent core structure 18 further comprises a layer of adhesive 120, for example typically a hot melt adhesive. This typically hot melt adhesive 120 serves to at least partially immobilize the absorbent polymer material 110. According to the present invention, the adhesive 120 can be typically a fiberized hot melt adhesive, i.e., being provided in fibres as a fibrous layer.

The storage layer comprises a cover layer 130 having respective first and second surface, positioned such that the second surface of the cover layer 130 can be in contact with the first surface of the layer of typically hot melt adhesive 120.

According to the present invention comprising e.g. a non-uniform layer of absorbent polymer material 110 the typically hot melt adhesive 120, for example typically provided as a fibrous layer, can be partially in contact with the absorbent polymer material 110 and partially in contact with the substrate layer 100. FIGS. 4, 5A and 5B show such a structure in an exemplary embodiment of the present invention. In this structure the layer of absorbent polymer material 110 is provided as a discontinuous layer, a layer of adhesive 120 is laid down onto the layer of absorbent polymer material 110, typically, for example, a layer of hot melt adhesive in fiberized form, such that the second surface of the layer of adhesive 120 can be in direct contact with the first surface of the layer of absorbent polymer material 110, but also in direct contact with the first surface of the substrate layer 100, where the substrate layer is not covered by the absorbent polymer material 110, i.e. typically in correspondence of the openings of the discontinuous layer of the absorbent polymer material 110. By saying "in direct contact", as well as more generally "in contact", as used herein, in contrast to more generally saying "facing", it is meant that there is no further intermediate component layer between e.g. the layer of adhesive 120 and the other respective layer in direct contact thereto, such as for example a further fibrous layer. It is however not excluded that a further adhesive material can be comprised between the layer of adhesive 120 and the cover layer 130, or the layer of absorbent polymer material 110 or, more typically, the substrate layer 100, such as for example a supplementary adhesive material provided onto the first surface of the substrate layer 100 to further stabilize the overlying absorbent polymer material 110. "In direct contact" and "in contact" can hence be considered to comprise in this context a direct adhesive contact between the layer of hot melt adhesive 120 and another respective layer as explained above, or more in general direct and, typically, adhesive contact between two layers, e.g. the layer of absorbent polymer material and the substrate layer. This imparts an essentially three-dimensional structure to the fibrous layer of hot melt adhesive 120 which in itself is essentially a two-dimensional structure of relatively small thickness (in z-direction), as compared to the extension in x- and y-direction. In other words, the layer of adhesive 120 undulates between the first surface of the absorbent polymer material 110 and the first surface of the substrate layer 100. The areas where the layer of adhesive 120 is in direct contact with the substrate layer 100, when present according to an embodiment of the present invention, are the areas of junction 140.

Thereby, in such an embodiment the adhesive 120 can provide spaces to hold the absorbent polymer material 110 typically towards the substrate layer 100, and can thereby immobilize this material. In a further aspect, the adhesive 120 can bond to the substrate layer 100 thus affixing the absorbent polymer material 110 to the substrate layer 100. Typical hot melt adhesive materials can also penetrate into both the absorbent polymer material 110 and the substrate layer 100, thus providing for further immobilization and affixation.

In the embodiment of FIGS. 5A-B portions of the cover layer 130 bond to portions of the substrate layer 100 via the adhesive 120. Thereby, the substrate layer 100 together with the cover layer 130 can provide spaces to immobilize the absorbent polymer material 110.

Of course, while the typically hot melt adhesive materials disclosed herein can provide a much improved wet immobilization, i.e. immobilization of absorbent polymer material when the article is wet or at least partially loaded, these hot melt adhesive materials can also provide a very good immobilization of absorbent polymer material when the article is dry.

In accordance with the present invention, the absorbent polymer material 110 may also be optionally mixed with fibrous material, which can provide a matrix for further immobilization of the absorbent polymer material. However, typically a relatively low amount of fibrous material can be used, for example less than about 40 weight %, less than about 20 weight %, or less than about 10 weight % of the total weight of the absorbent polymer material 110, positioned within the areas of absorbent polymer material.

According to the present invention, in a typically discontinuous layer of absorbent polymer material 110 the areas of absorbent polymer material can be connected to one another, while the areas of junction 140 can be areas, which in an embodiment may correspond to the openings in the discontinuous layer of absorbent polymer material, as shown for example in FIG. 4. The areas of absorbent polymer material are then referred to as connected areas. In an alternative embodiment, the areas of junction 140 can be connected to one another. Then, the absorbent polymer material can be deposited in a discrete pattern, or in other words the absorbent polymer material represents islands in a sea of adhesive 120. Hence, in summary, a discontinuous layer of absorbent polymer material 110 may comprise connected areas of absorbent polymer material 110, as e.g. illustrated in FIG. 4, or may alternatively comprise discrete areas of absorbent polymer material 110.

The present invention, and for example the embodiments described with reference to FIGS. 4, 5A and 5B can be typically used to provide the absorbent core of an absorbent article, as illustrated in FIG. 1. In that case, no further materials wrapping the core, such as for example a top layer and a bottom layer are being used. With reference to the embodiment of FIGS. 4, 5A and 5B the optional cover layer 130 may provide the function of a top layer and the substrate layer 100 may provide the function of a bottom layer of an absorbent core, wherein top and bottom layers respectively correspond to the body facing and garment facing surfaces of the absorbent core structure 18 in an absorbent article.

With reference to FIGS. 4, 5A and 5B, according to exemplary embodiments of the present invention, the areas of direct contact between the adhesive 120 and the substrate layer 100 are referred to as areas of junction 140. The shape, number and disposition of the areas of junction 140 will influence the immobilization of the absorbent polymer material 110. The areas of junction can be for example of squared, rectangular or circular shape. Areas of junction of circular shape can have a diameter of more than 0.5 mm, or more than 1 mm, and of less than 10 mm, or less than 5 mm, or less than 3 mm, or less than 2 mm, or less than 1.5 mm. If the areas of junction 140 are not of circular shape, they can be of a size as to fit inside a circle of any of the diameters given above.

The areas of junction 140, when present, can be disposed in a regular or irregular pattern. For example, the areas of junction 140 may be disposed along lines as shown in FIG. 4. These lines may be aligned with the longitudinal axis of the absorbent core, or alternatively they may have a certain angle in respect to the longitudinal edges of the core. A disposition along lines parallel with the longitudinal edges of the absorbent core structure 18 might create channels in the longitudinal direction which can lead to a lesser wet immobilization, hence for example the areas of junction 140 can be arranged along lines which form an angle of about 20 degrees, or about 30 degrees, or about 40 degrees, or about 45 degrees with the longitudinal edges of the absorbent core structure 18. Another pattern for the areas of junction 140 can be a pattern comprising polygons, for example pentagons and hexagons or a combination of pentagons and hexagons. Also typical can be irregular patterns of areas of junction 140, which also can give a good wet immobilization. Irregular patterns of areas of junction 140 can also give a better fluid handling behavior in case of absorption of menses or blood or vaginal discharges, since fluid can start diffusing in whichever direction from any initial acquisition point with substantially the same probability of contacting the absorbent polymer material in the e.g. discontinuous layer. Conversely, regular patterns might create preferential paths the fluid could follow with lesser probability of actually contacting the absorbent polymer material.

According to the present invention the layer of adhesive 120 can comprise any suitable adhesive material. Typically, the layer of adhesive 120 can comprise any suitable hot melt adhesive material.

The absorbent articles detailed herein may also have integrated or attached cuffs (e.g., incontinence articles with barrier leg cuffs attached to the longitudinal edges of the article). The leg cuffs may take the form of absorbent article leg cuffs known in the art. In one non-limiting example, the article can have leg cuffs as described in U.S. Patent Publication No. 2011/0319855 A1.

The sanitary napkin 10 can have a fluid acquisition/distribution layer 20 beneath the topsheet 14, and serves to rapidly draw discharged body fluids, in particular menstrual fluids and/or urine, through the adjacent permeable (primary) topsheet 14. This allows the surface of the topsheet 14 adjacent the wearer of the article to remain relatively clean and dry (it also provides acquisition/distribution functions).

The Fluid Acquisition/Distribution Layer

The fluid acquisition/distribution layer, as described below, comprises of three or more stratums integrated together so that they cannot be manually separated. The fluid acquisition/distribution layer is substantially free of airlaid materials. Each stratum maintains its unique properties for at least a portion of the stratum along the z-direction, even when integrated into a larger fluid acquisition/distribution layer. Unlike prior core systems that rely on layering materials, Applicants have found that by integrating a plurality of stratums, one can create fluid acquisition/distribution layer that acts differently upon the fluid as it travels in the Z direction while improving the manner in which the fluid transitions between stratums due to the integration of fibers. The fluid acquisition/distribution layer provides capillary suction to "pull" fluid through the topsheet 14, which is competing for trickle/low flow conditions. The fluid acquisition/distribution layer 20 also can contain a gush by providing distribution functions to efficiently utilize the absorbent core structure 18, as well as provide intermediate storage until the absorbent core structure 18 can accept fluid.

Each stratum of the fluid acquisition/distribution layer exhibits a pore size distribution that contributes to the overall pore size distribution of the fluid acquisition/distribution layer. Pore size distribution can be expressed in a pore volume ratio parameter and/or the pore volume factor, which is measured as detailed below in the methods section. In some embodiments of the articles detailed herein, the pore volume ratio can be greater than about 6, or greater than about 8, or greater than about 10. The pore volume factor can be greater than about 500 mm$^3$/µm·g. In some forms, the pore volume factor may be greater than about 600 mm$^3$/µm·g or greater than about 700 mm$^3$/µm·g or greater than about 800 mm$^3$/µm·g or about 900 mm$^3$/µm·g. In some forms, the pore volume factor may be between about 500 mm$^3$/µm·g to about 900 mm$^3$/µm·g or from about 600 mm$^3$/µm·g to about 800 mm$^3$/µm·g specifically including all values within these ranges and any ranges created thereby. Pore size distribution can also be expressed in a pore volume radius mode, which is measured as detailed in the methods herein. In some embodiments of the articles detailed herein, the pore volume radius mode can be between about 60 µm and about 120 µm, or between about 65 µm and about 105 µm, or between about 70 µm and about 90 µm.

The fluid acquisition/distribution layer has a first surface and a second surface. Between the first surface and the second surface, the fluid acquisition/distribution layer comprises of three or more stratums along the Z-direction. The fluid acquisition/distribution layer does not contain adhesives, latex, and pulp. The fluid acquisition/distribution layer can have a basis weight of up to 175 grams per square meter (gsm); or a basis weight of up to 150 gsm; or a basis weight in the range of about 30 gsm to about 150 gsm; or in the range of about 45 gsm to about 150 gsm; or in the range of about 45 gsm to about 135 gsm; or in the range of about 55 gsm to about 125 gsm, or in a range of about 50 gsm to about 75 gsm including any values within these ranges and any ranges created thereby.

The fluid acquisition/distribution layer can have a caliper of between 2.0 millimeters (mm) and 4.0 mm; between 2.25 mm and 3.75 mm; between 2.5 mm and 3.5 mm; or between 2.5 mm and 3.0 mm including any values within these ranges and any ranges created thereby.

The fluid acquisition/distribution layer can also have a cross machine direction (CD) flexural rigidity of about 0.01 mN·cm to about 20 mN·cm. In some embodiments, the fluid acquisition/distribution layer has a CD flexural rigidity of about 0.05 mN·cm to about 10 mN·cm or from about 0.07 mN·cm to about 1.0 mN·cm or from about 0.08 mN·cm to about 0.3 mN·cm including any values within these ranges and any ranges created thereby. In some embodiments, the fluid acquisition/distribution layer has a MD flexural rigidity of less than about 4.8 mN·cm. In some embodiments, the MD flexural rigidity can be greater than about 0.59 mN·cm. The MD flexural rigidity can be from about 0.60 mN·cm to about 3 mN cm specifically including all values within this range and all ranges created thereby.

As noted previously, it may be desirable to have stiffness and flexural rigidity in the CD to reduce bunching while maintaining comfort and body fit. For this reason, in some forms, it may be beneficial for the flexural rigidity in the CD to be close to the flexural rigidity of the MD. In some embodiments, the CD flexural rigidity/MD flexural rigidity can be between about 10% to about 50% or from about 5.2% to about 7.3%, specifically including all values within these ranges and all ranges created thereby.

The carded staple fiber nonwoven of the fluid acquisition/distribution layer 20 can be manufactured from an assortment of suitable fiber types that produce the desired mechanical performance and fluid handling performance. In some embodiments, the carded staple fiber nonwoven may be formed from a combination of stiffening fibers, absorbing fibers and filler fibers. The stiffening fibers, for example, can form about 10% to about 50%, by weight, of the carded staple fiber nonwoven. For some example fluid acquisition/distribution layers, the stiffening fibers can form about 15% to 75%, by weight, of the carded staple fiber nonwoven. In other embodiments, the stiffening fibers can form about 25%, by weight, of the carded staple fiber nonwoven.

As a total, stiffening fibers can be up to 85% of the fluid acquisition/distribution layer. Stiffening fibers can be between 10% and 100% of a stratum within the fluid acquisition/distribution layer, such as, for example, 20% of a stratum within the fluid acquisition/distribution layer, 30% of a stratum within the fluid acquisition/distribution layer, 40% of a stratum within the fluid acquisition/distribution layer, 50% of a stratum within the fluid acquisition/distribution layer, 60% of a stratum within the fluid acquisition/distribution layer, 70% of a stratum within the fluid acquisition/distribution layer, 80% of a stratum within the fluid acquisition/distribution layer, 90% of a stratum within the fluid acquisition/distribution layer, or 100% of a stratum within the fluid acquisition/distribution layer.

Absorbent fibers can be up to 50% of the fluid acquisition/distribution layer. Absorbent fibers can be between 10% and 100% of a stratum within the fluid acquisition/distribution layer, such as, for example, 20% of a stratum within the fluid acquisition/distribution layer, 30% of a stratum within the fluid acquisition/distribution layer, 40% of a stratum within the fluid acquisition/distribution layer, 50% of a stratum within the fluid acquisition/distribution layer, 60% of a stratum within the fluid acquisition/distribution layer, 70% of a stratum within the fluid acquisition/distribution layer, 80% of a stratum within the fluid acquisition/distribution layer, 90% of a stratum within the fluid acquisition/distribution layer, or 100% of a stratum within the fluid acquisition/distribution layer.

The stiffening fibers can be polyethylene terephthalate (PET) fibers, or other suitable non-cellulosic fibers known in the art. For carded staple fiber nonwovens including PET fibers, the PET fibers can have a dtex in the range of about 1.5 to about 15.0, or in the range of about 6.0 to about 12.0. The staple length of the stiffening fibers can be in the range of about 28 mm to about 100 mm, or in the range of about 37 mm to about 50 mm. Some carded staple fiber nonwovens include stiffening fibers with a staple length of about 38 mm to 42 mm. The PET fibers can have any suitable structure or shape. For example, the PET fibers can be round or have other shapes, such as spiral, scalloped oval, trilobal, scalloped ribbon, and so forth. Further, the PET fibers can be solid, hollow or multi-hollow. In some embodiments of the carded staple fiber nonwoven, the stiffening fibers may be fibers made of hollow/spiral PET. Optionally, the stiffening fibers may be spiral-crimped or flat-crimped. The stiffening fibers may have a crimp value of between about 4 and about 12 crimps per inch (cpi), or between about 4 and about 8 cpi, or between about 5 and about 7 cpi, or between about 9 and about 10 cpi. Particular non-limiting examples of stiffening fibers can be obtained from Wellman, Inc. Ireland under the trade names H1311 and T5974. Other examples of suitable stiffening fibers for utilization in the carded staple fiber nonwovens detailed herein are disclosed in U.S. Pat. No. 7,767,598 to Schneider et al.

As described above, the fluid acquisition/distribution layer comprises of three or more stratums. The ratio of fibers described above may be different for each stratum. Once integrated, the stratums form one heterogeneous structure that cannot be separated.

Other suitable examples of stiffening fibers include polyester/co-extruded polyester fibers. The stiffening fibers may be so-called bi-component fibers, where individual fibers are provided from different materials, usually a first and a second polymeric material. The two materials may be chemically different (hence the fibers are chemically heterogeneous) or they may differ only in their physical properties while being chemically identical (hence the fibers are chemically homogeneous). For example, may the intrinsic viscosity of the two materials be different, which has been found to influence the crimping behavior of the bi-component fibers. Bi-component fibers that are suitable as stiffening fibers are side-by-side bi-component fibers as disclosed for example in WO 99/00098. The stiffening fibers may also be a blend of bi-component fibers with polyester fibers.

With specific reference to bicomponent fibers comprised of a polypropylene/polyethylene fiber composition, in a cross-sectional view of a fiber, the material with a higher softening temperature can provide the central part (i.e, the core) of the fiber. The core typically is responsible for the bicomponent fiber's ability to transmit forces and have a certain rigidity or otherwise provide structures with resiliency. The outer coating on the core (i.e., the sheath) of the fiber can have a lower melting point and is used to facilitate thermally bonding of substrates comprising such fibers. In one embodiment, a polypropylene core is provided with a polyethylene coating on the outside, such that about 50%, by weight, of the fiber material is polypropylene and 50%, by weight, of the fiber material is polyethylene. Other quantitative amounts can of course be selected. For example, bicomponent fibers can have a composition from about 30% to about 70%, by weight, polyethylene, while others have about 35% to about 65%, by weigh polyethylene. In some embodiments, bicomponent fibers can have a composition from about 40% to about 60% or about 45% to about 55%, by weight, polyethylene.

Another suitable bi-component stiffening fiber is a fiber of circular cross section with a hollow space in the centre that is spiral crimped. It is preferred that 10-15% of the cross sectional area are hollow, more preferably 20-30% of the cross sectional area are hollow. Without wishing to be bound by theory, it is believed that the spiral crimping of fibers is beneficial for their liquid acquisition and distribution behaviour. It is assumed that the spiral crimp increases the void space in an acquisition member formed by such fibers. Often, an absorbent article, when being worn, is exposed to a certain pressure exerted by the wearer, which potentially decreases the void space in the acquisition member. Having good permeability and sufficient void space available are important for good liquid distribution and transport. It is further believed that the bi-component spiral-crimped fibers as described above are suitable to maintain sufficient void volume even when an acquisition member is exposed to pressure. Also, spiral-crimped fibers believed to provide for good permeability as for a given fiber dtex value, the hollow fiber cross-section allows for a larger outer diameter of the fiber as compared to a compact cross-section. The outer diameter of a fiber appears to determine the permeability behavior of an acquisition member formed by such fibers.

The absorbing fibers, for example, can form about 10% to about 50%, by weight, of the carded staple fiber nonwoven. For some example fluid acquisition/distribution layers, the absorbing fibers can form about 30% to about 40%, by weight, of the carded staple fiber nonwoven. In other embodiments, the absorbing fibers can form about 35%, by weight, of the carded staple fiber nonwoven. Within a stratum, they may be up to 100% of the individual stratum.

The absorbing fibers can be rayon, such as viscose rayon, or other suitable cellulosic fibers known in the art, such as cotton (or a blend of these fibers). For carded staple fiber nonwovens including rayon, the rayon can have a dtex in the range of about 1.0 to about 8.0, or from about 2.0 to about 6.0. The staple length of the absorbing fibers can be in the range of about 20 mm to about 100 mm, or about 30 mm to about 50 mm or about 35 mm to about 45 mm. The rayon fibers can have any suitable structure or shape. The rayon fibers may be a blend of any suitable structures and shapes. For example, the rayon fibers can be round or have other shapes, such as spiral, scalloped oval, trilobal, other multilobal shapes, scalloped ribbon, and so forth. Further, the rayon fibers can be solid, hollow or multi-hollow. In some embodiments of the carded staple fiber nonwoven, the absorbing fibers may be trilobal in shape, or another shape with a multiple lobes in cross section. Other examples of suitable multi-lobed absorbing fibers for utilization in the carded staple fiber nonwovens detailed herein are disclosed in U.S. Pat. No. 6,333,108 to Wilkes et al, U.S. Pat. No. 5,634,914 to Wilkes et al., and U.S. Pat. No. 5,458,835 to Wilkes et al.

One advantage of multiple lobed absorbing fibers is their greater bulk over single-limbed fibers, because the circumferential area of the multiple lobed fibers is larger than their actual cross-sectional area. For example, Japanese Patent Application Kokai 61-113812 describes a filament yarn consisting of X- or Y-shaped continuous viscose filaments that is used in textile applications where bulk is important, for example in pile weaves. Another advantage of multi-limbed absorbing fibers is their increased absorbency over single-limbed fibers.

The filler fibers, for example, can form about 1% to about 80%, by weight, of the carded staple fiber nonwoven. For some example fluid acquisition/distribution layers, the filler fibers can form about less than about 60%, by weight, of the carded staple fiber nonwoven. In other embodiments, the filler fibers can form about 40%, by weight, of the carded staple fiber nonwoven. Filler fibers may be placed in any stratum of the fluid acquisition/distribution layer. For example, filler fibers may be located in the topmost layer to help with capillary suction of fluid from the topsheet into the absorbent structure.

The filler fibers can be any thermoplastic fiber, such as polypropylene (PP), or other suitable thermoplastic fibers known in the art. For carded staple fiber nonwovens including thermoplastic fibers, the fibers can have a dtex of greater than about 1.0. Some carded staple fiber nonwovens can include PP having a dtex in the range of about 4 to about 10. The staple length of the filler fibers can be in the range of about 20 mm to about 100 mm, or about 30 mm to about 50 mm or about 35 mm to about 45 mm. The thermoplastic fibers can have any suitable structure or shape. For example, the thermoplastic fibers can be round or have other shapes, such as spiral, scalloped oval, trilobal, scalloped ribbon, and so forth. Further, the PP fibers can be solid, hollow or multi-hollow. In some embodiments of the carded staple fiber nonwoven, the third filler fibers may be solid and round in shape. Other suitable examples of filler fibers include polyester/co-extruded polyester fibers. Additionally, other suitable examples of filler fibers include bi-component fibers such as polyethylene/polypropylene, polyethylene/polyethylene terephthalate, polypropylene/polyethylene terephthalate. These bi-component fibers may be configured as a sheath and a core. The bi-component fibers may provide a cost effective way to increase basis weight of the material while additionally enabling optimization of the pore size distribution.

The carded staple fiber nonwoven of the fluid acquisition/distribution layer 20 formed in accordance with the present disclosure imparts a number of desirable physical properties, including its narrow pore size distribution, wicking/capillarity, permeability, wet Z-direction crush resistance and flexural rigidity. Generally, the absorbing fibers of the carded staple fiber nonwoven, such as rayon, provide capillarity, which serves to transport fluid from the topsheet 14 to the absorbent core structure 18. The stiffening fibers of the carded staple fiber nonwoven, such as PET, provide Z-direction strength to prevent, or at least limit, collapse of the fluid acquisition/distribution layer 20 when wetted while also providing desirable permeability. The filler fibers of the carded staple fiber nonwoven, such as polypropylene fibers, serve to provide a cost effective way to increase basis weight of the material while having minimal effect on pore size distribution.

The secondary storage layer can have a smaller cross direction width than the fluid acquisition/distribution layer. The secondary storage layer can have a smaller cross direction length than the fluid acquisition/distribution layer. The secondary storage layer can have a cross direction width that is a percent of the fluid acquisition/distribution layer cross direction width, such as, for example, 90% of the fluid acquisition/distribution layer cross direction width, 80% of the fluid acquisition/distribution layer cross direction width, 70% of the fluid acquisition/distribution layer cross direction width, 60% of the fluid acquisition/distribution layer cross direction width, 50% of the fluid acquisition/distribution layer cross direction width, 40% of the fluid acquisition/distribution layer cross direction width, 30% of the fluid acquisition/distribution layer cross direction width, 20% of the fluid acquisition/distribution layer cross direction width, or 10% of the fluid acquisition/distribution layer cross direction width. The secondary storage layer can have a cross direction length that is a percent of the fluid acquisition/distribution layer cross direction length, such as, for example, 90% of the fluid acquisition/distribution layer cross direction length, 80% of the fluid acquisition/distribution layer cross direction length, 70% of the fluid acquisition/distribution layer cross direction length, 60% of the fluid acquisition/distribution layer cross direction length, 50% of the fluid acquisition/distribution layer cross direction length, 40% of the fluid acquisition/distribution layer cross direction length, 30% of the fluid acquisition/distribution layer cross direction length, 20% of the fluid acquisition/distribution layer cross direction length, or 10% of the fluid acquisition/distribution layer cross direction length. If the fluid acquisition/distribution layer is any shape other than a rectangle, the width and length used to calculate the percent is the longest width and length of the acquisition/distribution layer.

The fluid acquisition/distribution layer can exhibit desirable parameters in terms of Mean pore value, capillary work potential, wicking ratios, and plane permeability ratios. Because one can integrate different stratums with tailored properties each having unique parameters, the fluid acquisition/distribution layer can exhibit different parameters within a layer having each stratum tailored to a desired parametric range so that the overall layer functions in a tailored manner.

TABLE 1

| Embodiment 1 | Gsm | Viscose Trilobal 3.3 | Viscose 1.7 round | 7 PET/CoPET | 5.8 PE/PET Concentric Bico | 10 HS PET | 3.3 PET |
|---|---|---|---|---|---|---|---|
| Stratum 1 | 30 | 30% | 70% | | | | |
| Stratum 2 | 30 | | | | 30% | 45% | 25% |
| Stratum 3 | 40 | | | | 30% | 45% | 25% |
| Stratum 4 | 40 | | | | 30% | 45% | 25% |

| Embodiment 2 | Gsm | Viscose Trilobal 3.3 | Viscose 1.7 round | 7 PET/CoPET | 5.8 PE/PET Concentric Bico | 10 HS PET |
|---|---|---|---|---|---|---|
| Stratum 1 | 30 | 30% | 70% | | | |
| Stratum 2 | 30 | | | 50% | | 50% |
| Stratum 3 | 40 | | | 50% | | 50% |
| Stratum 4 | 40 | | | 50% | | 50% |

As shown in Table 1, the upper layer of each embodiment (stratum 1) includes viscose in combination with tri-lobal fibers. Applicants have found that by including viscose fibers (tri-lobal, round, or combinations of tri-lobal and round) one can create an acquisition/distribution layer that has an absorbent outer layer which can quickly wick fluid.

The subsequent layers including Polyethylene/Coextruded polyethylene, Polyethylene/terathalate allow for fluid to pass through the structure to the wicking layer thus allowing the fluid to be wicked by the lower layer(s) in the product. This is enabled by placing a higher level of viscose in the stratum that serves as the lower stratum of the acquisition/distribution layer in the absorbent article. Additionally, the acquisition/distribution layer may have a gradient level of viscose in each stratum thereby allowing wicking to increase per stratum.

Further, the fluid continuity and integration of the layers such that they are integrated is enabled by the fiber lengths. Unlike other traditional air-laid layers, the embodiments above utilize the fiber length(s) to integrate the different stratums thereby creating the fluid acquisition/distribution layer with the desirable properties.

As shown in Table 1 and Table 2, a fluid acquisition/distribution layer may include three or more stratum. Each stratum may have a different composition, gsm, or other properties. The stratums are integrated to create a single fluid acquisition/distribution layer. Applicants have found that by integrating three or more stratum without the use of adhesives, one can create a layer that has higher basis weight allowing for improved comfort in the form of improved flexibility and loftness while not hindering fluid acquisition and absorption. Additionally, without being held by theory, it is believed that the higher basis weight without the use of adhesives in the integrated layer has improved rewet in comparison to non integrated materials that have similar basis weight. As such, without being bound by theory, the acquisition/distribution layer allows for better leakage protection, flexibility, and rewet protection while delivering parallel absorbency and acquisition by delivering a new structure that lies in a new area of performance.

Additionally, without being bound by theory, it is believed that by placing higher permeability in the top layers and high wicking in the lower layers, one can create an acquisition/distribution layer that will take in the fluid while reducing the stain size caused by the menses passing through the acquisition/distribution layer. This is unlike a homogenous construction, wherein the stain would be consistent and larger. Instead, by allowing the fluid to be pulled vertically instead of laterally, the stain size can be reduced.

TABLE 2

|  | GSM | Viscose 1.3 | Viscose 1.7 | Viscose 3.3 | 7 PET/CoPET | HS PET 10 |
|---|---|---|---|---|---|---|
| Embodiment #3 | | | | | | |
| Stratum 1 | 30 | | 35% | 30% | | 35% |
| Stratum 2 | 30 | | 10% | | 45% | 45% |
| Stratum 3 | 40 | | 10% | | 45% | 45% |
| Stratum 4 | 40 | | 10% | | 45% | 45% |
| Embodiment #4 | | | | | | |
| Stratum 1 | 30 | | 45% | 40% | | 15% |
| Stratum 2 | 30 | | 30% | | 35% | 35% |
| Stratum 3 | 40 | | 10% | | 45% | 45% |
| Stratum 4 | 40 | | 10% | | 45% | 45% |
| Embodiment #5 | | | | | | |
| Stratum 1 | 30 | 35% | | 30% | | 35% |
| Stratum 2 | 30 | 30% | | | 35% | 35% |
| Stratum 3 | 40 | 30% | | | 35% | 35% |
| Stratum 4 | 40 | 30% | | | 35% | 35% |

As shown in Table 2, one can include cellulose in the body facing stratum (stratum 4) by adding viscose. Without being bound by theory, the additional cellulose improves the connectivity between the upper stratum or body facing stratum and the lower stratums and may additionally improve the capillary suction of the upper stratum which first contacts the fluid.

Additionally, it has been surprisingly found that while a small amount of cellulose leads to benefits in capillary suction and fluid connectivity, having a higher percentage of cellulose in the body facing stratum may lead to a collapse in caliper of the acquisition/distribution layer. This is exemplified by Embodiment 5 which contains 30% in the body facing stratum in the form of Viscose 1.3 and showed a collapse in caliper versus samples with little or no cellulose as shown in Table 3. All the embodiments of Tables 1, 2, and 3 listed in Table 3 where made using the same process parameters and have the same overall basis weight. As shown in Table 3, a small increase of 20% cellulose (from 10% to 30%) in the body facing stratum may lead to an overall caliper drop of 1.4 millimeters versus Embodiment 2 which contains no viscose or cellulose or a drop in caliper of 42% while 10% viscose may lead to a drop in caliper of about 9% as shown by Embodiment 3. Unlike Embodiment 3, Embodiment 4 includes an increasing amount of cellulose from top to bottom unlike embodiments 3 and 5 which have a consistent percentage amount in the three stratums beginning with the body facing stratum.

TABLE 3

| Embodiment | Caliper |
|---|---|
| Embodiment 2 | 3.3 millimeters |
| Embodiment 3 | 3.0 millimeters |
| Embodiment 4 | 2.8 millimeters |
| Embodiment 5 | 1.9 millimeters |

Methods of Making Carded Staple Fiber Nonwovens

Figure 3:
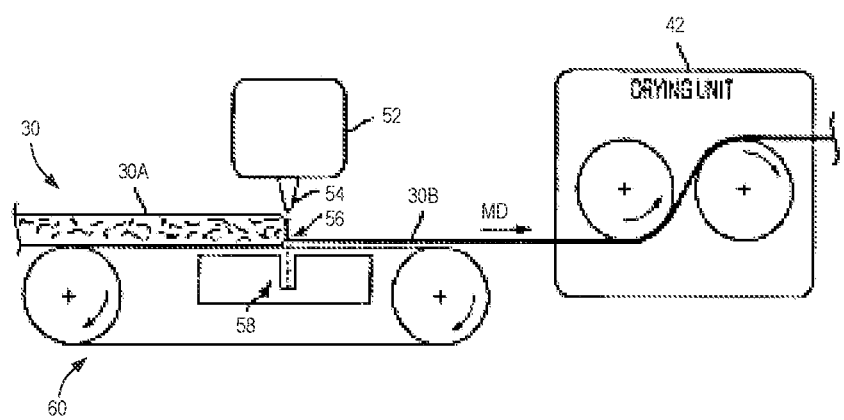
FIG. 3 depicts a simplified, schematic view of one example of a continuous carded staple fiber nonwoven manufacturing process.

FIG. 3 depicts a simplified, schematic view of one example of a continuous carded staple fiber nonwoven manufacturing process. As is to be appreciated, the carded staple fiber nonwoven produced by the process of FIG. 3 can be used in the manufacturing of a variety of absorbent articles, such as the sanitary napkin 10 of FIGS. 1-2, as well as a variety of other absorbent articles, including diapers, training pants, adult incontinence undergarments, and the like.

As is generally known in the art, hydroentanglement (sometimes referred to as spunlacing, jet entanglement, water entanglement, hydroentanglement or hydraulic needling), is a mechanical bonding process whereby fibers of a nonwoven web are entangled by means of high pressure water jets. Patterning can be achieved by use of patterned drums or belts which cause the fibers to form a negative image of the drum design in the fabric. The formed web of various fibrous components (usually airlaid, wetlaid, or carded, but sometimes spunbond or melt-blown, etc.) can first be compacted and prewetted to eliminate air pockets and then water-needled. With reference to FIG. 3, a fibrous structure 30 is formed from cellulosic fibers, non-cellulosic fibers and bicomponent fibers, e.g. filler fibers, absorbing fibers, and stiffening fibers. The fibrous structure 30 has an unbonded portion 30A upstream of a jet head 52 and a bonded (i.e., hydroentangled) portion 30B downstream of the jet head 52. During the entanglement process, the fibrous structure 30 is passed by the jet head 52 that comprises a plurality of injectors that are positioned to generally form a water curtain (for simplicity of illustration, only one injector 54 is illustrated in FIG. 3). A water jet 56 is directed through the fibrous structure 30 at high pressures, such as 25 or 400 bar. As is to be appreciated, while not illustrated, multiple rows of injectors 54 are typically used, which can be positioned on one or both sides of the fibrous structure 30.

The fibrous structure 30 can be supported by any suitable support system 60, such as a moving wire screen (as illustrated) or on a rotating porous drum, for example. While not illustrated, it is to be appreciated that hydroentanglement systems can expose the fibrous structure 30 to a series of jet heads 52 along the machine direction, with each delivering water jets at different pressures. The particular number of jet heads 52 utilized can be based on, for example, desired basis weight, degree of bonding required, characteristics of the web, and so forth. As the water jet 56 penetrates the web, a suction slot 58 positioned proximate beneath the fibrous structure 30 collects the water so that it can be filtered and returned to the jet head 52 for subsequent injection. The water jet 56 delivered by the jet head 52 exhausts most of its kinetic energy primarily in rearranging fibers within the fibrous structure 30 to turn and twist the fibers to form a series of interlocking knots.

Once the fibrous structure 30 has been hydroentangled (shown as bonded portion 30B), the hydroentangled fibrous structure 30B is then passed through a dewatering device where excess water is removed. In the process illustrated in FIG. 3, the dewatering device is a drying unit 42. The drying unit 42 can be any suitable drying system, such as a multi-segment multi-level bed dryer, a vacuum system, and/or an air drum dryer, for example. The drying unit 42, or other dewatering device, serves to substantially dry the hydroentangled fibrous structure 30B. The term "substantially dry" is used herein to mean that the hydroentangled fibrous structure 30B has a liquid content, typically water or other solution content, less than about 10%, less than about 5%, or less than about 3%, by weight.

The fibrous structure can be heat stiffened. The fibrous structure can be heat stiffened at temperatures between 125 degrees Celsius and 160 degrees Celsius; between 130 degrees Celsius and 145 degrees Celsius; between 132 degrees Celsius and 142 degrees Celsius; or between 138 degrees Celsius and 142 degrees Celsius specifically including all values within these ranges and any ranges created thereby.

Once the hydroentangled fibrous structure 30B is substantially dry, the hydroentangled fibrous structure 30B can be heated to an elevated temperature. By heating the hydroentangled fibrous structure 30B to a particular temperature, or temperature range, the flexural rigidity of the fibrous structure can be increased (i.e., stiffened). Stiffening the fibrous structure results in a number of desired results. For example, the increase of stiffness of the hydroentangled fibrous structure 30B allows the structure to tolerate the subsequent manufacturing processes. Additionally, when the hydroentangled fibrous structure 30B is subsequently incorporated into an absorbent article, such as sanitary napkin 10, for example, cross machine direction (CD) bunching is reduced, leading to less leakage and more comfort for a wearer.

By introducing additional heat to the hydroentangled fibrous structure 30B to raise its temperature during the thermal bonding process, the sheath of the bicomponent fibers will first begin to soften. As these softened bicomponent fibers touch each other, bonds will form between the sheaths, thereby increasing the overall flexural rigidity of the structure due to the formation of these bond sites. The elevated temperature of the hydroentangled fibrous structure 30B is not high enough, however, to cause other types of fibers within the hydroentangled fibrous structure to flow or otherwise soften, bond, or collapse. The formation of the bond sites within the hydroentangled fibrous structure 30B adds to the stiffness of the web, yet the fluid handling performance of the hydroentangled fibrous structure 30B remains as desired. It will be recognized that raising the final drying stage temperature (or otherwise introducing heat to the hydroentangled fibrous structure) to just above a softening temperature of a portion of the bicomponent fiber provides an increase in mechanical performance while also maintaining liquid handling performance. If, however, the hydroentangled fibrous structure is heated to too high of temperature, the rigidity of the structure increases and the liquid handling performance of the structure can suffer.

Once the hydroentangled fibrous structure 30B is manufactured in accordance with the present disclosure it can be incorporated into, for example, an absorbent material. With regard to the sanitary napkin 10 of FIGS. 1-2, the fluid acquisition/distribution layer 20 incorporating the hydroentangled fibrous structure 30B can be bonded to, or otherwise attached to the topsheet 14. In some embodiments, thermal point calendaring or other suitable bonding is utilized. In other embodiments, the hydroentangled fibrous structure 30B can serve as an absorbent core of an absorbent article. For example, pantiliners and incontinence pads can be formed with the hydroentangled fibrous structure 30B positioned between a topsheet and a bottom sheet to function as at least part of an absorbent core, as described above with respect to FIGS. 1-2. Furthermore, in some embodiments, the hydroentangled fibrous structure 30B does not include a binder component.

The fibrous structure described above may be utilized to have multiple stratums available to one manufacturing system. Dependent upon the desired properties of the fluid acquisition/distribution layer, the system can selectively choose which stratums to utilize in the manufacturing of the fluid acquisition/distribution layer. In this manner, the system can create an array of fluid acquisition/distribution layers that vary in composition, thickness, and dependent upon the selection of stratums and manufacturing parameters, different fluid handling properties and different physical parameters such as, for example, pore size volume. For example, a fluid acquisition/distribution layer to be used with a film topsheet can have different properties from a fluid acquisition/distribution layer to be used with a nonwoven topsheet. This can be achieved while still maintaining the desirable targeted z-direction compressibility.

A. A carded staple fiber nonwoven comprising three or more stratums, the carded staple fiber nonwoven having a basis weight of up to about 175 gsm, the carded staple fiber nonwoven comprising a blend of absorbing fibers, stiffening fibers and filler fibers, wherein the carded staple fiber nonwoven is heat stiffened and wherein the three or more stratums are integrated without adhesives.

B. The carded staple fiber nonwoven of paragraph A, wherein the carded staple fiber nonwoven has a caliper of between about 2 mm and about 4 mm.

C. The carded staple fiber nonwoven of any of paragraphs A-B, wherein the carded staple fiber nonwoven has a caliper of between about 2 mm to about 3 mm.

D. The carded staple fiber nonwoven of any of paragraphs A-C, wherein the carded staple fiber nonwoven has a basis weight of between about 45 gsm to about 150 gsm.

E. The carded staple fiber nonwoven of any of paragraphs A-D, wherein the carded staple fiber nonwoven has an MD flexural rigidity of between about 0.01 mN cm to about 20 mN·cm.

F. The carded staple fiber nonwoven of any of paragraphs A-E, wherein the carded staple fiber nonwoven has a pore volume ratio of greater than about 8.

G. The carded staple fiber nonwoven of any of paragraphs A-F, wherein the stiffening fibers comprise hollow, spiral fibers formed from polyethylene terephthalate (PET), wherein the stiffening fibers have a linear density of between about 6 dtex and about 15 dtex.

H. The carded staple fiber nonwoven of any of paragraphs A-G, wherein the absorbing fibers comprise tri-lobal fibers formed from rayon, wherein the absorbing fibers have a linear density of between about 1 dtex and about 6 dtex.

I. The carded staple fiber nonwoven of any of paragraphs A-H, wherein the filler fibers comprise solid, round fibers formed from polypropylene (PP), wherein the filler fibers have a linear density of about 3 dtex or greater.

J. The carded staple fiber nonwoven of any of paragraphs A-I, wherein the stiffening fibers form about 10% to about 50%, by weight, of the carded staple fiber nonwoven.

K. The carded staple fiber nonwoven of any of paragraphs A-J, wherein the absorbing fibers form about 10% to about 50%, by weight, of the carded staple fiber nonwoven.

L. The carded staple fiber nonwoven of any of paragraphs A-K, wherein the filler fibers form about between about 1% to about 80%, by weight, of the carded staple fiber nonwoven.

M. An absorbent article comprising a topsheet, a backsheet, and an absorbent core, the absorbent core comprising the carded staple fiber nonwoven of any of paragraphs A-L.

AA. An array of at least two absorbent articles, the array comprising a first absorbent article having a first topsheet and a first fluid acquisition/distribution layer comprising of three or more stratums, and a second absorbent article comprising a second topsheet, and a second fluid acquisition/distribution layer comprising of three or more stratums, wherein the first topsheet does has a different composition than the second topsheet.

BB. The array of paragraph AA, wherein the first topsheet comprises a nonwoven.

CC. The array of absorbent articles according to any of paragraphs AA-BB, wherein the first topsheet comprises a film.

DD. The array of absorbent articles according to any of paragraphs AA-CC, wherein the first fluid acquisition/distribution layer comprises A carded staple fiber nonwoven having a basis weight of up to about 175 gsm, the carded staple fiber nonwoven comprising a blend of absorbing fibers, stiffening fibers and filler fibers, wherein the carded staple fiber nonwoven is heat stiffened and wherein the three or more stratums are integrated without adhesives.

EE. The array of absorbent articles according to any of paragraphs AA-DD, wherein the second fluid acquisition/distribution layer comprises a carded staple fiber nonwoven having a basis weight of up to about 175 gsm, the carded staple fiber nonwoven comprising a blend of absorbing fibers, stiffening fibers and filler fibers, wherein the carded staple fiber nonwoven is heat stiffened and wherein the three or more stratums are integrated without adhesives.

FF. The array of absorbent articles according to any of paragraphs AA-EE, wherein the first fluid acquisition/distribution layer has a caliper of between about 2 mm and about 4 mm.

GG. The array of absorbent articles according to any of paragraphs AA-FF, wherein the first fluid acquisition/distribution layer has a caliper of between about 2 mm to about 3 mm.

HH. The array of absorbent articles according to any of paragraphs AA-GG, wherein the first fluid acquisition/distribution layer has three stratums and the second acquisition/distribution layer has four or more stratums.

II. The array of absorbent articles according to any of paragraphs AA-HH, wherein the first fluid acquisition/distribution layer has a basis weight of between about 45 grams per square meter (gsm) to about 150 gsm.

JJ. The array of absorbent articles according to any of paragraphs AA-II, wherein the first fluid acquisition/distribution layer has an MD flexural rigidity of between about 0.01 mN cm to about 20 mN·cm.

KK. The array of absorbent articles according to any of paragraphs AA-JJ, wherein the first fluid acquisition/distribution layer has a pore volume ratio of greater than about 8.

LL. The array of absorbent articles according to any of paragraphs AA-KK, wherein the first fluid acquisition/distribution layer comprises stiffening fibers comprising hollow, spiral fibers formed from polyethylene terephthalate (PET), wherein the stiffening fibers have a linear density of between about 6 decitex (dtex) and about 15 dtex.

MM. The array of absorbent articles according to any of paragraphs AA-LL, wherein the first fluid acquisition/distribution layer comprises absorbing fibers comprising tri-lobal fibers formed from rayon, wherein the absorbing fibers have a linear density of between about 2 dtex and about 6 dtex.

NN. The array of absorbent articles according to any of paragraphs AA-MM, wherein the first fluid acquisition/distribution layer comprises filler fibers comprising solid, round fibers formed from polypropylene (PP), wherein the filler fibers have a linear density of about 3 dtex or greater.

OO. The array of absorbent articles according to any of paragraphs AA-NN, wherein the first fluid acquisition/distribution layer comprises stiffening fibers form about 10% to about 50%, by weight, of the first fluid acquisition/distribution layer.

PP. The array of absorbent articles according to any of paragraphs AA-OO, wherein the first fluid acquisition/distribution layer comprises absorbing fibers form about 10% to about 50%, by weight, of the first fluid acquisition/distribution layer.

QQ. The array of absorbent articles according to any of paragraphs AA-PP, wherein the first fluid acquisition/distribution layer comprises filler fibers form about between about 1% to about 80%, by weight, of the first fluid acquisition/distribution layer.

Test Methods

The following test methods were used.

(1). The measurements for fiber linear density provided herein were obtained by using the Standard Test Method for Linear Density of Textile Fibers, as detailed in ASTM Designation D1577-07.

(2). The measurements for fiber lengths provided herein were obtained by using the Standard Test Method for Length and Length Distribution of Manufactured Staple Fibers (Single-Fiber Test), as detailed in ASTM Designation D5103-07.

(3). The measurements for capacity provided herein were obtained by using Worldwide Strategic Partners (WSP) Test Method 10.1.

(4). The measurements for caliper provided herein were obtained by using Worldwide Strategic Partners (WSP) Test Method 120.6 using a 0.5 kpa load. For the later tested samples a 50.8 mm anvil diameter was used at 1.43 kilo pascals (kPa) load, 0.3 inches/second drop speed and 2 second dwell time.

(5). The measurements for MD bending length and CD bending length provided herein were obtained by using Worldwide Strategic Partners (WSP) Test Method 90.5. For the later tested samples, note that samples sizes were utilized which were 25 mm by at least 85 mm.

(6). The measurements for air permeability provided herein were obtained by using Worldwide Strategic Partners (WSP) Test Method 70.1. For the later tested samples a pressure drop of 125 Pa and an orifice 38.3 square centimeters was used.

(7). The measurements for basis weight provided herein were obtained by using Worldwide Strategic Partners (WSP) Test Method 130.1.

(8). The measurements for pore volume radius mode and pore volume ratio provided herein were obtained by the following method regarding pore volume distribution.

Pore Volume Distribution

Pore volume distribution measurements are made on a TRI/Autoporosimeter (TRI/Princeton Inc. of Princeton, N.J.) The TRI/Autoporosimeter is an automated computer-controlled instrument for measuring pore volume uptake and pore-size distribution in porous materials. Here, measurements are performed on an initially dry sample using a 0.25 psi confining pressure during an absorption, desorption and second absorption cycle. Pores between 5 micron (m) and 1000 m are measured. Information on the TRI/Autoporosimeter, its operation and data treatments can be found in The Journal of Colloid and Interface Science 162(1994), pp. 163-170, incorporated here by reference.

Figure 6:
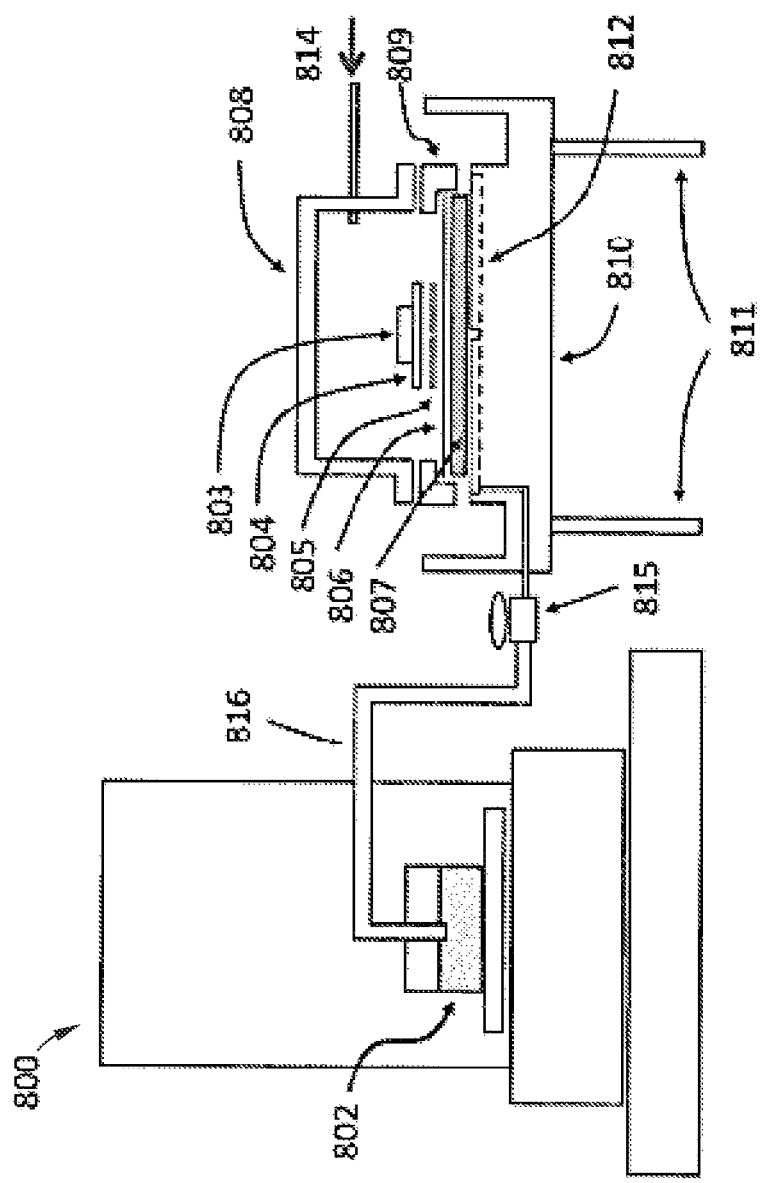
FIG. 6 depicts a schematic view of the equipment used to measure pore volume distribution.
Figure 7:
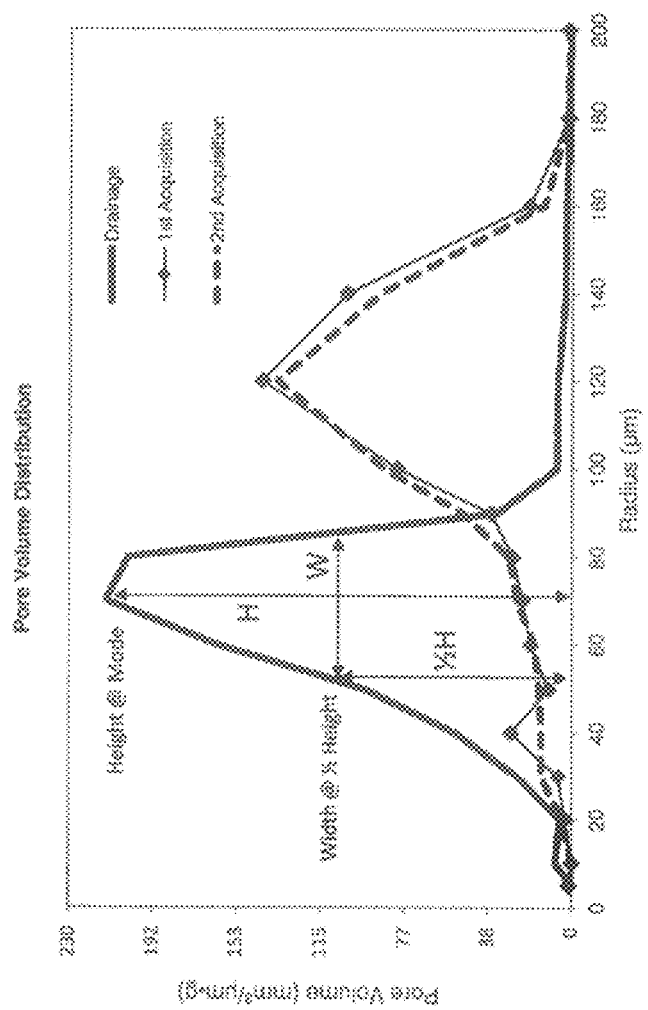
FIG. 7 depicts an example of a chart illustrating a pore volume distribution experiment cycle.

A representation of the TRI equipment is shown in FIG. 6 and consists of a balance 800 with fluid reservoir 802 which is in direct fluid communication with the sample 805 which resides in a sealed, air-pressurized sample chamber 810. An example experiment cycle is shown in FIG. 7.

Determining the Pore Volume Uptake or Pore-Size Distribution involves recording the increment of liquid that enters or leaves a porous material as the surrounding air pressure is altered. A sample in the test chamber is exposed to precisely controlled changes in air pressure. As the air pressure increases or decreases, the void spaces or pores of the porous media de-water or uptake fluid, respectively. Total fluid uptake is determined as the total volume of fluid absorbed by the porous media.

Pore-Size Distribution can further be determined as the distribution of the volume of uptake of each pore-size group, as measured by the instrument at the corresponding pressure. The pore size is taken as the effective radius of a pore and is related to the pressure differential by the following relationship.

Pressure differential=$[2\gamma \cos \Theta)]$/effective radius where $\gamma$=liquid surface tension, and $\Theta$=contact angle For this experiment: $\gamma$=27 dyne/cm$^2$ divided by the acceleration of gravity; cos $\Theta$=1°

The automated equipment operates by precisely changing the test chamber air pressure in user-specified increments, either by decreasing pressure (increasing pore size) to cause fluid uptake by the porous media, or by increasing pressure (decreasing pore size) to de-water the porous media. The liquid volume absorbed (drained) at each pressure increment yields the pore size distribution. The fluid uptake is the cumulative volume for all pores taken up by the porous media, as it progresses to saturation (e.g. all pores filled).

Experimental Conditions:

Take a 9 cm diameter, 0.22 m membrane filter (mixed cellulose esters, Millipore GSWP, EMD Millipore Corp., Billerica MA) by adhering the filter to a 9 centimeter diameter by 0.6 cm thick Monel porous frit 807 using KRYLON® spray paint (FilmTools Gloss White Spray Paint #1501). Allow the frit/membrane to dry before use.

Fill the inner base 812 of the sample chamber with hexadecane (available from Sigma-Aldrich CAS #544-76-3). Place the frit 807 membrane side up onto the base of the sample chamber 810, and secure it into place with a locking collar 809. Fill the connecting tube 816, reservoir 802, and the frit 807 with hexadecane assuring that no bubbles are trapped within the connecting tube or the pores within the frit and membrane. Using the legs of the base 811, level the sample chamber and align the membrane with the top surface of the fluid within the reservoir.

Dye cut a sample 5.5 cm square. Measure the mass of the sample to the nearest 0.1 mg. A 5.5 cm square, Plexiglas cover plate 804 and confining weight 803 are selected to provide a confining pressure of 0.25 psi.

Place the top 808 of the sample chamber in place and seal the chamber. Apply the appropriate air pressure to the cell (via connection 814) to achieve a 5 μm effective pore radius. Close the liquid valve 815. Open the sample chamber, place the sample 805, cover plate 804 and confining weight 803 into the chamber onto the membrane 806 and seal the chamber. Open the liquid valve 815 to allow free movement of liquid to the balance.

Progress the system through a sequence of pore sizes (pressures) as follows (effective pore radius in m): 5, 10, 20, 30, 40, 50, 60, 70, 80, 90, 100, 120,140, 160, 180, 200, 250, 300, 350,400, 450, 500, 550, 600, 700, 800, 1000, 800, 700, 600, 550, 500, 450, 400, 350, 300, 250, 200, 180, 160, 140, 120, 100, 90, 80, 70, 60, 50, 40, 30, 20, 10, 5, 10, 20, 30, 40, 50, 60, 70, 80, 90, 100, 120,140, 160, 180, 200, 250, 300, 350,400, 450, 500, 500, 550, 600, 700, 800, 1000. The sequence is progressed to the next radius when an equilibrium rate of less than 25 mg/min is measured at the balance.

In like fashion, measure the acquisition/drainage/acquisition cycle blank without a sample.

Based on the incremental volume values, calculate the blank-corrected values for cumulative volume versus equivalent pore radius.

Cumulative Volume (mm$^3$/mg)=[Specimen Fluid Uptake (mg)−Blank Fluid Uptake (mg)]/Density of Hexadecane (g/cm$^3$)/Sample Mass (mg)

Pore Volume (mm$^3$/μm·g)=Change in Effective Radius (μm)/[Change in Cumulative Volume (mm$^3$/mg)*1000]

Plot Pore Volume (mm$^3$/μm·g) vs. Effective Radius (μm). Referring to FIG. 7, determine from the drainage curve, the Pore Volume value (H) at the mode of the Effective Radius. Where a vertical line parallel to the Y-axis extending from the value (H) to the X-axis defines Pore Volume Radius Mode. From the peak calculate the width (W) at half height (½ H) by connecting the data points with straight lines and calculate the Pore Volume Ratio as H/W and report to the nearest 0.01 mm³/μm·g/μm.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

The invention claimed is:

1. A sanitary napkin comprising a topsheet, a backsheet, and an absorbent core, the absorbent core comprising a fluid acquisition/distribution layer and a fluid storage layer comprising particles of absorbent gelling material, wherein the fluid acquisition/distribution layer is a single integrated layer formed of a staple fiber nonwoven comprising a plurality of strata including a wearer-facing stratum and a garment facing stratum, the staple fiber nonwoven comprising a combination of staple fibers including bicomponent fibers and cellulosic fibers, wherein the cellulosic fibers are present in greater weight percentage in the garment-facing stratum and lesser weight percentage in the wearer-facing stratum; wherein the bicomponent fibers have a PE/PET sheath-core configuration; wherein the staple fiber nonwoven is heat stiffened, wherein at least a portion of individual ones of the bicomponent fibers are bonded together via bonds between sheaths thereof; wherein the cellulosic fibers and the bicomponent fibers are integrated within the single integrated layer, wherein the wearer facing stratum comprises from about 10% to about 50% by weight of cellulosic fibers and from about 10% to about 50% by weight of bicomponent fibers, wherein the garment facing stratum comprises greater than 60% of cellulosic fibers, and wherein the fluid acquisition/distribution layer has a caliper of between about 2 millimeters and about 4 millimeters and a basis weight of 100 gsm to 175 gsm.

2. A sanitary napkin comprising a backsheet, a fluid acquisition/distribution layer having a body facing surface and a garment facing surface and a fluid storage layer comprising particles of absorbent gelling material, wherein the fluid acquisition/distribution layer is a single integrated layer formed of a staple fiber nonwoven comprising a plurality of strata including a wearer-facing stratum and a garment facing stratum, the staple fiber nonwoven comprising a combination of staple fibers including bicomponent fibers and cellulosic fibers, wherein the cellulosic fibers are present in greater weight percentage in the garment-facing stratum and lesser weight percentage in the wearer-facing stratum; wherein the staple fiber nonwoven is heat stiffened such that at least a portion of individual ones of the bicomponent fibers are bonded together via bonds between sheaths thereof; wherein the cellulosic fibers and the bicomponent fibers are integrated within the single integrated layer; wherein the fluid acquisition/distribution layer has a caliper of between about 2 millimeters and about 4 millimeters and a basis weight of 100 gsm to 175 gsm, wherein the cellulosic fibers have a linear density of between about 1 dtex and about 6 dtex, wherein the bicomponent fibers have a linear density of between about 5 dtex to about 15 dtex, wherein the wearer facing stratum comprises from about 10% to about 50% by weight of cellulosic fibers and from about 10% to about 50% by weight of bicomponent fibers, and wherein the garment facing stratum comprises greater than 60% of cellulosic fibers.

3. The sanitary napkin of claim 1, wherein the carded staple fiber nonwoven has an MD flexural rigidity of between about 0.01 mN cm to about 20 mN·cm.

4. The sanitary napkin of claim 1, wherein the carded staple fiber nonwoven has a pore volume ratio of greater than about 8.

5. The sanitary napkin of claim 1, wherein the cellulosic fibers are rayon fibers.

6. The absorbent article of claim 1, wherein the carded staple fiber nonwoven comprising hollow, spiral fibers.

7. The absorbent article of claim 6, wherein the hollow, spiral fibers are formed from polyethylene terephthalate (PET).

8. The absorbent article of claim 6, wherein the hollow, spiral fibers have a linear density of between about 6 dtex and about 15 dtex.

9. The absorbent article of claim 1, wherein the cellulosic fibers comprise tri-lobal fibers formed from rayon having a linear density of between about 2 dtex and about 6 dtex.

10. The absorbent article of claim 1, wherein the carded staple fiber nonwoven comprising solid, round fibers formed from polypropylene.

11. The absorbent article of claim 1, wherein the carded staple fiber nonwoven comprises filler fibers, and wherein the wearer facing stratum comprises the filler fibers and the garment facing stratus comprises the filler fibers.

12. The absorbent article of claim 11, wherein a weight percentage of the filler fibers of the wearer facing stratum is greater than or equal to a weight percentage of the filler fibers of the garment facing stratum.

13. The absorbent article of claim 11, wherein the wearer facing stratum comprises less than about 60% by weight of the filler fibers.

14. The absorbent article of claim 11, wherein the garment facing stratum comprises less than about 40% by weight of the filler fibers.

15. The absorbent article of claim 11, wherein the filler fibers are made of at least one of polypropylene, polyethylene, and polyethylene terephthalate.

* * * * *